(12) United States Patent
Harada et al.

(10) Patent No.: US 6,916,592 B2
(45) Date of Patent: Jul. 12, 2005

(54) ESTERS, POLYMERS, RESIST COMPOSITIONS AND PATTERNING PROCESS

(75) Inventors: Yuji Harada, Niigata-ken (JP); Jun Hatakeyama, Niigata-ken (JP); Yoshio Kawai, Niigata-ken (JP); Masaru Sasago, Hirakata (JP); Masayuki Endo, Kishiwada (JP); Shinji Kishimura, Itami (JP); Kazuhiko Maeda, Tokyo (JP); Michitaka Ootani, Tokyo (JP); Haruhiko Komoriya, Kawagoe (JP)

(73) Assignees: Shin-Etsu Chemical Co., Ltd., Tokyo (JP); Matsushita Electric Industrial Co., Ltd., Kadoma (JP); Central Glass Co., Ltd., Ube (JP)

(*) Notice: Subject to any disclaimer, the term of this patent is extended or adjusted under 35 U.S.C. 154(b) by 0 days.

(21) Appl. No.: 10/395,268

(22) Filed: Mar. 25, 2003

(65) Prior Publication Data

US 2003/0219678 A1 Nov. 27, 2003

(30) Foreign Application Priority Data

Mar. 25, 2002 (JP) .......................................... 2002-083943
Mar. 25, 2002 (JP) .......................................... 2002-084093

(51) Int. Cl.$^7$ .......................... G03F 7/039; G03F 7/30; G03F 7/38; C08F 12/30; C08F 114/18
(52) U.S. Cl. .................. 430/270.1; 430/320; 430/322; 430/325; 430/326; 430/327; 430/905; 430/907; 430/910; 430/914; 526/243; 526/281; 526/282; 526/287; 526/286
(58) Field of Search ............................... 430/270.1, 320, 430/322, 325, 326, 327, 905, 907, 910, 914, 330; 526/243, 281, 282, 287, 286

(56) References Cited

U.S. PATENT DOCUMENTS

| | | | |
|---|---|---|---|
| 2,728,749 A | * 12/1955 | Coover, Jr. et al. | ......... 526/243 |
| 4,491,628 A | 1/1985 | Ito et al. | |
| 5,310,619 A | 5/1994 | Crivello et al. | |
| 5,972,559 A | * 10/1999 | Watanabe et al. | ......... 430/270.1 |
| 6,303,266 B1 | * 10/2001 | Okino et al. | ............. 430/270.1 |

FOREIGN PATENT DOCUMENTS

| | | |
|---|---|---|
| JP | 63-27829 A | 2/1988 |
| JP | 2-27660 B2 | 6/1990 |
| JP | 9-73173 A | 3/1997 |
| JP | 9-230595 A | 9/1997 |
| JP | 10-10739 A | 1/1998 |
| WO | WO 97/33198 A1 | 9/1997 |

OTHER PUBLICATIONS

Fujigaya, T., et al., "A New Photoresist Material for 157 nm Lithography", Journal of Photopolymer Science and Technology, vol. 15, No. 4, May 30, 2002, pp. 643–654.*

* cited by examiner

*Primary Examiner*—Richard L Schilling
(74) *Attorney, Agent, or Firm*—Birch, Stewart, Kolasch & Birch, LLP

(57) ABSTRACT

A resist composition comprising a base polymer having a fluorinated sulfonate or fluorinated sulfone introduced therein is sensitive to high-energy radiation, has excellent transparency, contrast and adherence, and is suited for lithographic microprocessing.

20 Claims, No Drawings

ESTERS, POLYMERS, RESIST COMPOSITIONS AND PATTERNING PROCESS

This invention relates to polymers useful as the base resin in resist compositions suited for microfabrication and sulfonic acid esters useful as the starting monomers for the polymers. It also relates to resist compositions, especially chemical amplification resist compositions comprising the polymers, and a patterning process using the same.

BACKGROUND OF THE INVENTION

In the drive for higher integration and operating speeds in LSI devices, the pattern rule is made drastically finer. The rapid advance toward finer pattern rules is grounded on the development of a projection lens with an increased NA, a resist material with improved performance, and exposure light of a shorter wavelength. To the demand for a resist material with a higher resolution and sensitivity, chemical amplification positive working resist materials which are catalyzed by acids generated upon light exposure are effective as disclosed in U.S. Pat. Nos. 4,491,628 and 5,310,619 (JP-B 2-27660 and JP-A 63-27829). They now become predominant resist materials especially adapted for deep UV lithography.

Also, the change-over from i-line (365 nm) to shorter wavelength KrF excimer laser (248 nm) brought about a significant innovation. Resist materials adapted for KrF excimer lasers enjoyed early use on the 0.30 micron process, passed through the 0.25 micron rule, and currently entered the mass production phase on the 0.18 micron rule. Engineers have started investigation on the 0.10 micron rule or less, with the trend toward a finer pattern rule being accelerated.

For ArF excimer laser (193 nm), it is expected to enable miniaturization of the design rule to 0.13 μm or less. Since conventionally used novolac resins and polyvinylphenol resins have very strong absorption in proximity to 193 nm, they cannot be used as the base resin for resists. To ensure transparency and dry etching resistance, some engineers investigated acrylic and alicyclic (typically cycloolefin) resins as disclosed in JP-A 9-73173, JP-A 10-10739, JP-A 9-230595 and WO 97/33198.

With respect to $F_2$ laser (157 nm) which is expected to enable further miniaturization to 0.10 μm or less, more difficulty arises in insuring transparency because it was found that acrylic resins which are used as the base resin for ArF are not transmissive to light at all and those cycloolefin resins having carbonyl bonds have strong absorption. It was also found that poly(vinyl phenol) which is used as the base resin for KrF has a window for absorption in proximity to 160 nm, so the transmittance is somewhat improved, but far below the practical level.

Since carbonyl groups and carbon-to-carbon double bonds have absorption in proximity to 157 nm as mentioned above, reducing the number of such units is contemplated to be one effective way for improving transmittance. It was recently found that the transmittance in the $F_2$ region is outstandingly improved by introducing fluorine atoms into base polymers.

It was reported in SPIE 2001, Proceedings 4345–31, "Polymer design for 157 nm chemically amplified resists" that in resist compositions comprising a copolymer of tert-butyl α-trifluoromethylacrylate with 5-(2-hydroxy-2,2-bistrifluoromethyl)ethyl-2-norbornene and a copolymer of tert-butyl α-trifluoromethylacrylate with 4-(2-hydroxy-2,2-bistrifluoromethyl)methylstyrene, the absorbance of the polymer at 157 nm is improved to about 3. However, these resins are still insufficient in transparency because it is believed that an absorbance of 2 or less is necessary to form a rectangular pattern at a film thickness of at least 2,000 Å through $F_2$ exposure.

SUMMARY OF THE INVENTION

An object of the invention is to provide a novel polymer having a high transmittance to vacuum ultraviolet radiation of up to 300 nm, especially $F_2$ (157 nm), $Kr_2$ (146 nm), KrAr (134 nm) and $Ar_2$ (126 nm) excimer laser beams, and useful as the base resin in a resist composition, and a novel sulfonic acid ester useful as the starting monomer for the polymer. Another object is to provide a resist composition, and especially a chemical amplification resist composition, comprising the polymer, and a patterning process using the same.

It has been found that when a polymer having a fluorinated sulfonate or fluorinated sulfone introduced therein is used as a base resin, the resulting resist composition, especially chemically amplified resist composition is drastically improved in contrast and adhesion without detracting from transparency.

In a first aspect, the present invention provides a sulfonate compound having the following general formula (1).

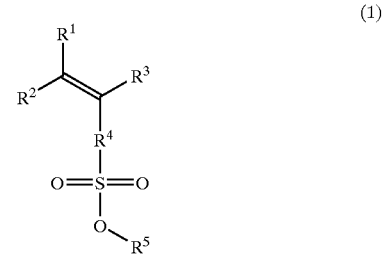

(1)

Herein $R^1$ to $R^3$ each are hydrogen, fluorine or a straight, branched or cyclic alkyl or fluorinated alkyl group of 1 to 20 carbon atoms, $R^4$ is a valence bond or a straight, branched or cyclic alkylene or fluorinated alkylene group of 1 to 20 carbon atoms, and $R^5$ is a straight, branched or cyclic fluorinated alkyl group of 1 to 30 carbon atoms.

The preferred sulfonate compound has the following general formula (1a).

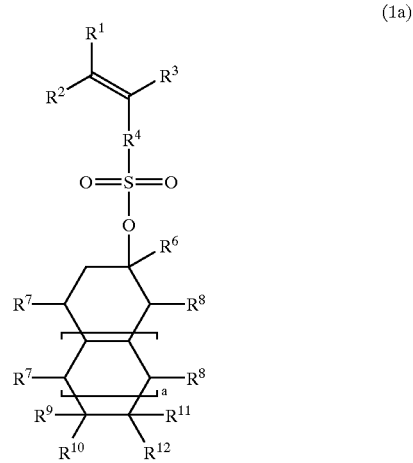

(1a)

Herein $R^1$ to $R^3$ each are hydrogen, fluorine or a straight, branched or cyclic alkyl or fluorinated alkyl group of 1 to 20 carbon atoms, $R^4$ is a valence bond or a straight, branched or cyclic alkylene or fluorinated alkylene group of 1 to 20 carbon atoms, $R^6$ to $R^8$ each are hydrogen, fluorine or a straight, branched or cyclic alkyl or fluorinated alkyl group of 1 to 20 carbon atoms, or $R^7$ and $R^8$ may bond together to form a ring, and in that event, each is an alkylene group of 1 to 20 carbon atoms which may contain a hetero atom such as oxygen, sulfur or nitrogen, $R^9$ to $R^{12}$ each are hydrogen, fluorine or a straight, branched or cyclic alkyl or fluorinated alkyl group of 1 to 20 carbon atoms, at least one of $R^9$ to $R^{12}$ containing at least one fluorine atom, or two of $R^9$ to $R^{12}$ may bond together to form a ring, and in that event, each is a straight, branched or cyclic alkylene or fluorinated alkylene group of 1 to 20 carbon atoms, and "a" is 0 or 1.

The preferred sulfonate compound has the following general formula (1b).

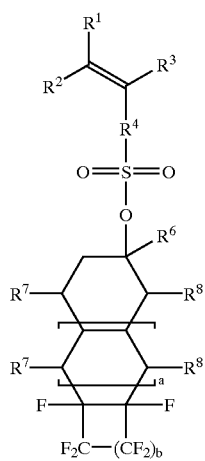

(1b)

Herein $R^1$ to $R^3$ each are hydrogen, fluorine or a straight, branched or cyclic alkyl or fluorinated alkyl group of 1 to 20 carbon atoms, $R^4$ is a valence bond or a straight, branched or cyclic alkylene or fluorinated alkylene group of 1 to 20 carbon atoms, $R^6$ to $R^8$ each are hydrogen, fluorine or a straight, branched or cyclic alkyl or fluorinated alkyl group of 1 to 20 carbon atoms, or $R^7$ and $R^8$ may bond together to form a ring, and in that event, each is an alkylene group of 1 to 20 carbon atoms which may contain a hetero atom such as oxygen, sulfur or nitrogen, "a" is 0 or 1, and "b" is an integer of 2 to 4.

In a second aspect, the present invention provides a polymer comprising recurring units of the following general formula (2) and having a weight average molecular weight of 1,000 to 500,000.

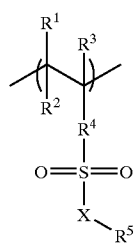

(2)

Herein $R^1$ to $R^3$ each are hydrogen, fluorine or a straight, branched or cyclic alkyl or fluorinated alkyl group of 1 to 20 carbon atoms, $R^4$ is a valence bond or a straight, branched or cyclic alkylene or fluorinated alkylene group of 1 to 20 carbon atoms, $R^5$ is a straight, branched or cyclic fluorinated alkyl group of 1 to 30 carbon atoms, and X is a valence bond or O.

The preferred polymer includes recurring units of the following general formula (2a).

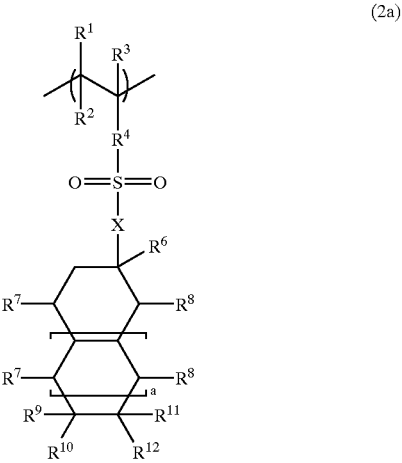

(2a)

Herein $R^1$ to $R^3$ each are hydrogen, fluorine or a straight, branched or cyclic alkyl or fluorinated alkyl group of 1 to 20 carbon atoms, $R^4$ is a valence bond or a straight, branched or cyclic alkylene or fluorinated alkylene group of 1 to 20 carbon atoms, $R^6$ to $R^8$ each are hydrogen, fluorine or a straight, branched or cyclic alkyl or fluorinated alkyl group of 1 to 20 carbon atoms, or $R^7$ and $R^8$ may bond together to form a ring, and in that event, each is an alkylene group of 1 to 20 carbon atoms which may contain a hetero atom such as oxygen, sulfur or nitrogen, $R^9$ to $R^{12}$ each are hydrogen, fluorine or a straight, branched or cyclic alkyl or fluorinated alkyl group of 1 to 20 carbon atoms, at least one of $R^9$ to $R^{12}$ containing at least one fluorine atom, or two of $R^9$ to $R^{12}$ may bond together to form a ring, and in that event, each is a straight, branched or cyclic alkylene or fluorinated alkylene group of 1 to 20 carbon atoms, "a" is 0 or 1, and X is a valence bond or O.

The preferred polymer has recurring units of the following general formula (2b).

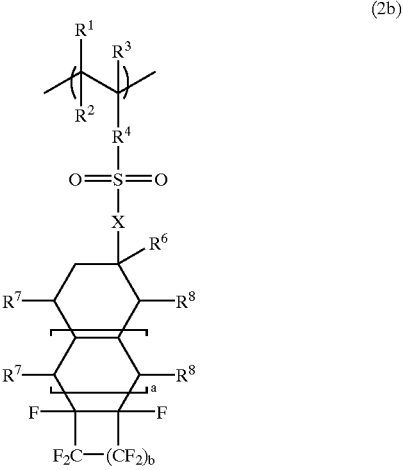

(2b)

Herein $R^1$ to $R^3$ each are hydrogen, fluorine or a straight, branched or cyclic alkyl or fluorinated alkyl group of 1 to 20 carbon atoms, $R^4$ is a valence bond or a straight, branched or cyclic alkylene or fluorinated alkylene group of 1 to 20 carbon atoms, $R^6$ to $R^8$ each are hydrogen, fluorine or a straight, branched or cyclic alkyl or fluorinated alkyl group of 1 to 20 carbon atoms, or $R^7$ and $R^8$ may bond together to form a ring, and in that event, each is an alkylene group of 1 to 20 carbon atoms which may contain a hetero atom such as oxygen, sulfur or nitrogen, "a" is 0 or 1, "b" is an integer of 2 to 4, and X is a valence bond or O.

In a preferred embodiment, the polymer includes recurring units of the following general formula (4a) or (4b).

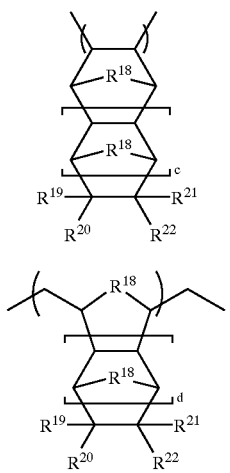

Herein $R^{18}$ is a methylene group, oxygen atom, sulfur atom or $SO_2$, $R^{19}$ to $R^{22}$ each are hydrogen, fluorine, a straight, branched or cyclic alkyl or fluorinated alkyl group of 1 to 20 carbon atoms or $-R^{23}-SO_2R^{24}$, at least one of $R^{19}$ to $R^{22}$ containing $-R^{23}-SO_2R^{24}$, $R^{23}$ is a valence bond or a straight, branched or cyclic alkylene or fluorinated alkylene group of 1 to 20 carbon atoms, $R^{24}$ is a straight, branched or cyclic fluorinated alkyl group of 1 to 20 carbon atoms, c is 0 or 1, and d is an integer of 0 to 2.

Typically, the polymer has a weight average molecular weight of 1,000 to 500,000.

In a preferred embodiment, the polymer further includes recurring units of the following general formula (5).

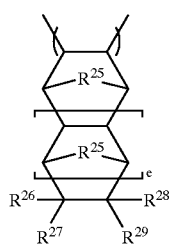

Herein $R^{25}$ is a methylene group, oxygen atom, sulfur atom or $SO_2$, $R^{26}$ to $R^{29}$ each are hydrogen, fluorine, $-R^{30}-OR^{31}$, $-R^{30}-CO_2R^{31}$ or a straight, branched or cyclic alkyl or fluorinated alkyl group of 1 to 20 carbon atoms, at least one of $R^{26}$ to $R^{29}$ containing $-R^{30}-OR^{31}$ or $-R^{30}-CO_2R^{31}$, $R^{30}$ is a valence bond or a straight, branched or cyclic alkylene or fluorinated alkylene group of 1 to 20 carbon atoms, $R^{31}$ is hydrogen, an acid labile group, adhesive group or a straight, branched or cyclic fluorinated alkyl group of 1 to 20 carbon atoms which may contain a hydrophilic group such as hydroxyl, and e is 0 or 1.

Preferably the recurring units of formula (5) have a structure of the following general formula (5a) or (5b).

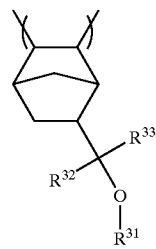

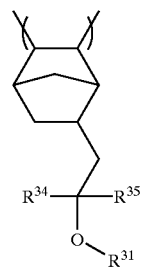

Herein $R^{31}$ is as defined above, $R^{32}$ to $R^{35}$ each are hydrogen, fluorine or an alkyl or fluorinated alkyl group of 1 to 4 carbon atoms, at least either one of $R^{32}$ and $R^{33}$ contains at least one fluorine atom, and at least either one of $R^{34}$ and $R^{35}$ contains at least one fluorine atom.

In a preferred embodiment, the polymer further includes recurring units of the following general formula (6).

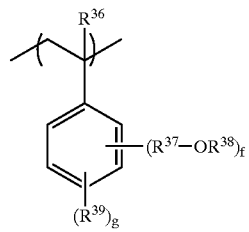

Herein $R^{36}$ is hydrogen, fluorine or a straight, branched or cyclic alkyl or fluorinated alkyl group of 1 to 20 carbon atoms, $R^{37}$ is a valence bond or a straight, branched or cyclic alkylene or fluorinated alkylene group of 1 to 20 carbon atoms, $R^{38}$ is hydrogen or an acid labile group, $R^{39}$ is fluorine or a straight, branched or cyclic fluorinated alkyl group of 1 to 20 carbon atoms, f is 1 or 2, and g is an integer of 0 to 4, satisfying $1 \leq f+g \leq 5$.

Preferably the recurring units of formula (6) have the following formula (6a) or (6b).

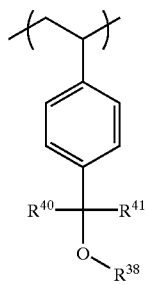

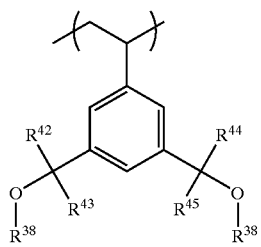

(6b)

Herein R[38] is as defined above, R[40] to R[45] each are hydrogen, fluorine or an alkyl or fluorinated alkyl group of 1 to 4 carbon atoms, at least either one of R[40] and R[41] contains at least one fluorine atom, at least either one of R[42] and R[43] contains at least one fluorine atom, and at least either one of R[44] and R[45] contains at least one fluorine atom.

In a further preferred embodiment, the polymer further includes recurring units of the following general formula (7).

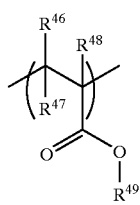

(7)

Herein R[46] to R[48] each are hydrogen, fluorine or a straight, branched or cyclic alkyl or fluorinated alkyl group of 1 to 20 carbon atoms, and R[49] is hydrogen, an acid labile group, an adhesive group or a straight, branched or cyclic fluorinated alkyl group of 1 to 20 carbon atoms which may contain a hydrophilic group such as hydroxyl. In formula (7), R[48] is typically trifluoromethyl.

In a third aspect, the invention provides a resist composition comprising the polymer defined above, preferably a chemically amplified positive resist composition comprising (A) the polymer defined above, (B) an organic solvent, and (C) a photoacid generator. The resist composition may further include (D) a basic compound and/or (E) a dissolution inhibitor.

In a fourth aspect, the invention provides a process for forming a resist pattern comprising the steps of applying the resist composition onto a substrate to form a coating; heat treating the coating and then exposing it to high-energy radiation in a wavelength band of 100 to 180 nm or 1 to 30 nm through a photomask; and optionally heat treating the exposed coating and developing it with a developer. The high-energy radiation is typically an $F_2$ laser beam, $Ar_2$ laser beam or soft x-ray.

DESCRIPTION OF THE PREFERRED EMBODIMENTS

Polymer

For improving the transmittance in proximity to 157 nm, reducing the number of carbonyl groups and/or carbon-to-carbon double bonds is contemplated to be one effective way. It was also found that introducing fluorine atoms into base polymers makes a great contribution to improved transmittance. In fact, poly(vinyl phenol) having fluorine introduced in its aromatic rings offers a transmittance nearly on a practically acceptable level (see JP-A 2001-146505). However, this base polymer was found to turn to be negative upon exposure to high-energy radiation as from an $F_2$ excimer laser, interfering with its use as a practical resist.

In contrast, those polymers obtained by introducing fluorine into acrylic resins or polymers containing in their backbone an alicyclic compound originating from a norbornene derivative were found to have a high transparency and eliminate the negative turning problem. However, an increased rate of introduction of fluorine into a resin to enhance the transparency thereof tends to compromise the adhesion of resin to substrate or the penetration of a developer. The present invention has succeeded in overcoming the above-described deficiencies without detracting from transparency, by introducing into a base polymer a fluorinated sulfonate or fluorinated sulfone featuring a relatively high transmittance at about 157 nm, excellent substrate adhesion and developer penetration.

According to the invention, using polymers or high molecular weight compounds comprising recurring units of the following general formulae (2), (2a), (2b), (2'), (4a) or (4b), resist compositions can be formulated which have improved substrate adhesion and developer penetration while maintaining high transparency at 157 nm.

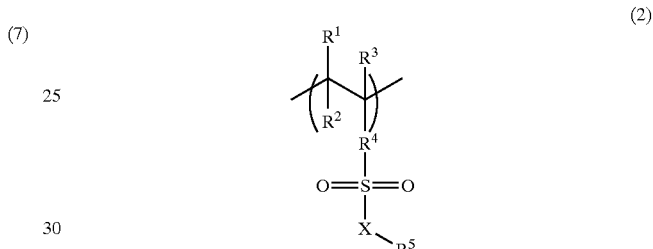

(2)

(2a)

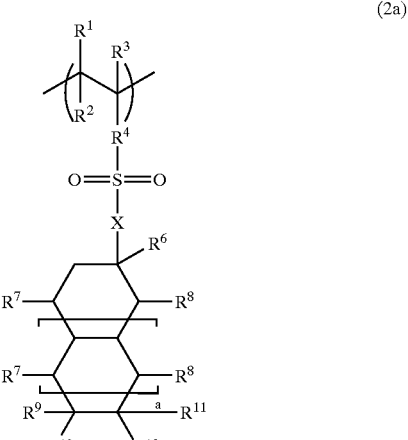

(2b)

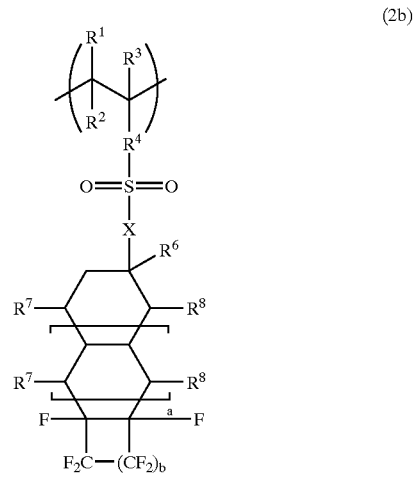

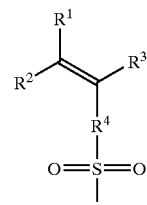
(1)

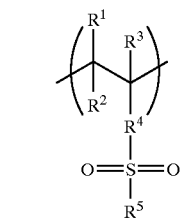
(2')

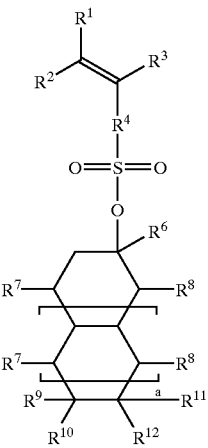
(1a)

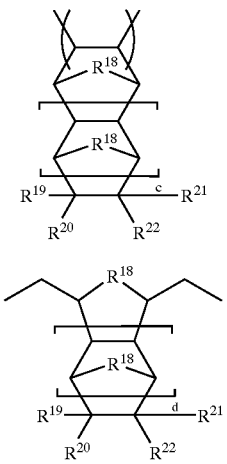
(4a)

(4b)

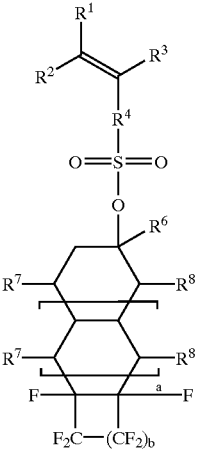
(1b)

Herein R¹ to R³ each are a hydrogen atom, a fluorine atom or a straight, branched or cyclic alkyl or fluorinated alkyl group of 1 to 20 carbon atoms. R⁴ is a valence bond or a straight, branched or cyclic alkylene or fluorinated alkylene group of 1 to 20 carbon atoms. R⁵ is a straight, branched or cyclic fluorinated alkyl group of 1 to 30 carbon atoms.

R⁶ to R⁸ each are a hydrogen atom, a fluorine atom or a straight, branched or cyclic alkyl or fluorinated alkyl group of 1 to 20 carbon atoms. R⁷ and R⁸ may bond together to form a ring, and in that event, each is an alkylene group of 1 to 20 carbon atoms which may contain a hetero atom such as oxygen, sulfur or nitrogen. R⁹ to R¹² each are a hydrogen atom, a fluorine atom or a straight, branched or cyclic alkyl or fluorinated alkyl group of 1 to 20 carbon atoms. At least one of R⁹ to R¹² should contain at least one fluorine atom. Two of R⁹ to R¹² may bond together to form a ring, and in that event, each is a straight, branched or cyclic alkylene or fluorinated alkylene group of 1 to 20 carbon atoms.

R¹⁸ is a methylene group, an oxygen atom, a sulfur atom or SO₂. R¹⁹ to R²² each are a hydrogen atom, a fluorine atom, a straight, branched or cyclic alkyl or fluorinated alkyl group of 1 to 20 carbon atoms or —R²³—SO₂R²⁴. At least one of R¹⁹ to R²² should contain —R²³—SO₂R²⁴. R²³ is a valence bond or a straight, branched or cyclic alkylene or fluorinated alkylene group of 1 to 20 carbon atoms. R²⁴ is a straight, branched or cyclic fluorinated alkyl group of 1 to 20 carbon atoms. The subscript "a" is 0 or 1, b is an integer of 2 to 4, c is 0 or 1, and d is an integer of 0 to 2. X is a valence bond or an oxygen atom (O).

It is noted that those polymers of formulae (2), (2a) and (2b) wherein X is O can be prepared by polymerizing sulfonic acid esters (simply sulfonates) of the following general formulae (1), (1a) and (1b), respectively.

Herein R¹ to R¹², a and b are as defined above.

More particularly, suitable straight, branched or cyclic alkyl groups of 1 to 20 carbon atoms include, but are not limited to, methyl, ethyl, propyl, isopropyl, n-propyl, n-butyl, sec-butyl, tert-butyl, cyclopentyl, cyclohexyl, cyclohexylmethyl, 2-ethylhexyl, n-octyl, 2-adamantyl, and (2-adamantyl)methyl, with those of 1 to 12 carbon atoms, especially 1 to 10 carbon atoms being preferred. Suitable straight, branched or cyclic alkyl groups of 1 to 30 carbon atoms include, but are not limited to, methyl, ethyl, propyl, isopropyl, n-propyl, n-butyl, sec-butyl, tert-butyl, cyclopentyl, cyclohexyl, cyclohexylmethyl, 2-ethylhexyl, n-octyl, 2-adamantyl, and (2-adamantyl)methyl, with those of 1 to 12 carbon atoms, especially 1 to 10 carbon atoms being preferred.

The fluorinated alkyl groups correspond to the foregoing alkyl groups in which some or all of the hydrogen atoms are replaced by fluorine atoms. Examples include, but are not limited to, trifluoromethyl, 2,2,2-trifluoroethyl, 3,3,3-trifluoropropyl, 1,1,1,3,3,3-hexafluoroisopropyl, and 1,1,2, 2,3,3,3-heptafluoropropyl as well as groups of the following formulae.

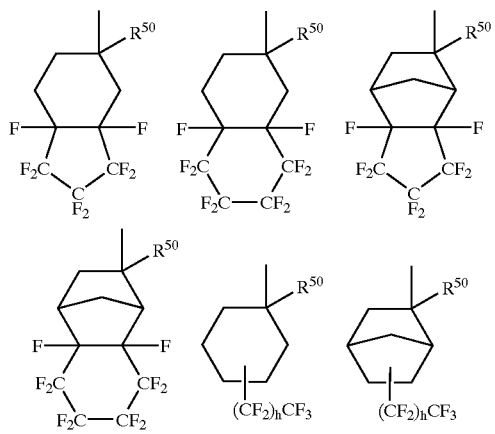

Herein, $R^{50}$ is a hydrogen atom, a fluorine atom or a straight, branched or cyclic alkyl or fluorinated alkyl group of 1 to 10 carbon atoms, and h is an integer of 0 to 5.

Suitable straight, branched or cyclic alkylene groups of 1 to 20 carbon atoms correspond to the foregoing alkyl groups with one hydrogen atom eliminated. Suitable fluorinated alkylene groups are similar alkylene groups which are partially or entirely substituted with fluorine atoms.

The acid labile groups represented by $R^{31}$, $R^{38}$ and $R^{49}$ are selected from a variety of such groups, preferably from among the groups of the following formulae (8) to (10).

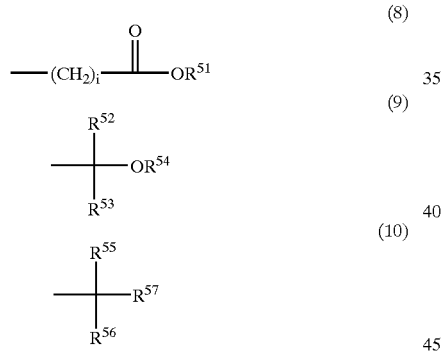

In formula (8), $R^{51}$ is a tertiary alkyl group of 4 to 20 carbon atoms, preferably 4 to 15 carbon atoms, or an oxoalkyl group of 4 to 20 carbon atoms. Suitable tertiary alkyl groups include tert-butyl, tert-amyl, 1,1-diethylpropyl, 1-ethylcyclopentyl, 1-butylcyclopentyl, 1-ethylcyclohexyl, 1-butylcyclohexyl, 1-ethyl-2-cyclopentenyl, 1-ethyl-2-cyclohexenyl, and 2-methyl-2-adamantyl. Suitable oxoalkyl groups include 3-oxocyclohexyl, 4-methyl-2-oxooxan-4-yl, and 5-methyl-5-oxooxolan-4-yl. Letter i is an integer of 0 to 6.

Illustrative, non-limiting, examples of the acid labile group of formula (8) include tert-butoxycarbonyl, tert-butoxycarbonylmethyl, tert-amyloxycarbonyl, tert-amyloxycarbonylmethyl, 1,1-diethylpropyloxycarbonyl, 1,1-diethylpropyloxycarbonylmethyl, 1-ethylcyclopentyloxycarbonyl, 1-ethylcyclopentyloxycarbonylmethyl, 1-ethyl-2-cyclopentenyloxycarbonyl, 1-ethyl-2-cyclopentenyloxycarbonylmethyl, 1-ethoxyethoxycarbonylmethyl, 2-tetrahydropyranyloxycarbonylmethyl, and 2-tetrahydrofuranyloxycarbonylmethyl groups.

In formula (9), $R^{52}$ and $R^{53}$ are hydrogen or straight, branched or cyclic alkyl groups of 1 to 18 carbon atoms, preferably 1 to 10 carbon atoms, for example, methyl, ethyl, propyl, isopropyl, n-butyl, sec-butyl, tert-butyl, cyclopentyl, cyclohexyl, 2-ethylhexyl and n-octyl. $R^{54}$ is a monovalent hydrocarbon group of 1 to 18 carbon atoms, preferably 1 to 10 carbon atoms, which may contain a hetero atom such as oxygen, for example, straight, branched or cyclic alkyl groups and substituted ones of these alkyl groups in which some hydrogen atoms are substituted with hydroxyl, alkoxy, oxo, amino or alkylamino groups. Exemplary substituted alkyl groups are shown below.

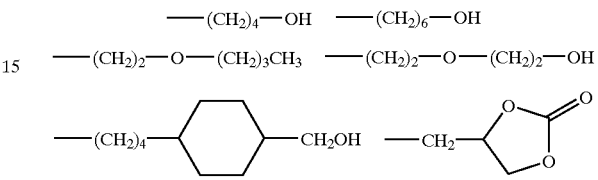

A pair of $R^{52}$ and $R^{53}$, a pair of $R^{52}$ and $R^{54}$, or a pair of $R^{53}$ and $R^{54}$ may bond together to form a ring. Each of $R^{52}$, $R^{53}$ and $R^{54}$ is a straight or branched alkylene group of 1 to 18 carbon atoms, preferably 1 to 10 carbon atoms, when they form a ring.

Of the acid labile groups of formula (9), straight or branched ones are exemplified by the following groups.

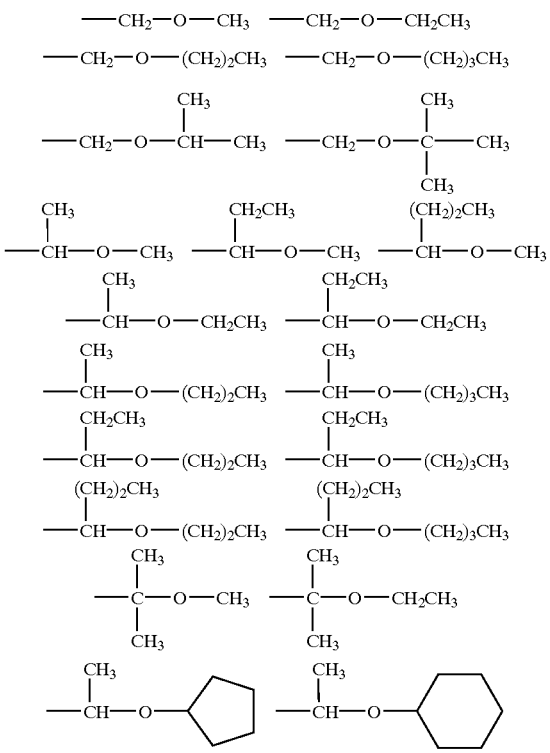

Of the acid labile groups of formula (9), cyclic ones are exemplified by tetrahydrofuran-2-yl, 2-methyltetrahydrofuran-2-yl, tetrahydropyran-2-yl, and 2-methyltetrahydropyran-2-yl.

Of the groups of formula (9), ethoxyethyl, butoxyethyl and ethoxypropyl are preferred.

In formula (10), $R^{55}$, $R^{56}$ and $R^{57}$ each are a monovalent hydrocarbon group, typically a straight, branched or cyclic alkyl group of 1 to 20 carbon atoms, which may contain a hetero atom such as oxygen, sulfur, nitrogen or fluorine. A pair of $R^{55}$ and $R^{56}$, $R^5$ and $R^{57}$, and $R^{56}$ and $R^{57}$, taken together, may form a ring with the carbon atom to which they are bonded.

Examples of the tertiary alkyl group represented by formula (10) include tert-butyl, triethylcarbyl, 1-ethylnorbornyl, 1-methylcyclohexyl, 1-ethylcyclopentyl, 2-(2-methyl)adamantyl, 2-(2-ethyl)adamantyl, tert-amyl, 1,1,1,3,3,3-hexafluoro-2-methyl-isopropyl, and 1,1,1,3,3,3-hexafluoro-2-cyclohexyl-isopropyl as well as the groups shown below.

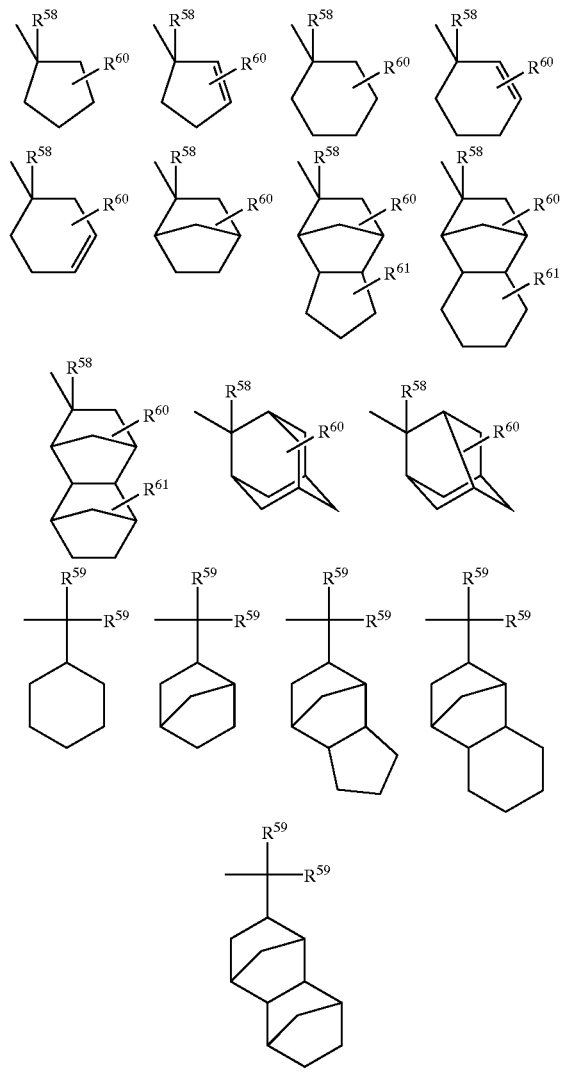

Herein, $R^{58}$ is a straight, branched or cyclic alkyl group of 1 to 6 carbon atoms, such as methyl, ethyl, propyl, isopropyl, n-butyl, sec-butyl, n-pentyl, n-hexyl, cyclopropyl, cyclopropylmethyl, cyclobutyl, cyclopentyl and cyclohexyl. $R^{59}$ is a straight, branched or cyclic alkyl group of 2 to 6 carbon atoms, such as ethyl, propyl, isopropyl, n-butyl, sec-butyl, n-pentyl, n-hexyl, cyclopropyl, cyclopropylmethyl, cyclobutyl, cyclopentyl and cyclohexyl. Each of $R^{60}$ and $R^{61}$ is hydrogen, a monovalent hydrocarbon group of 1 to 6 carbon atoms which may contain a hetero atom, or a monovalent hydrocarbon group of 1 to 6 carbon atoms which may be separated by a hetero atom. These groups may be straight, branched or cyclic. The hetero atom is typically selected from oxygen, sulfur and nitrogen atoms and may be contained or intervene in the form of —OH, —OR$^{62}$, —O—, —S—, —S(=O)—, —NH$_2$, —NHR$^{62}$, —N(R$^{62}$)$_2$, —NH— or —NR$^{62}$— wherein $R^{62}$ is a $C_{1-5}$ alkyl group. Examples of $R^{60}$ and $R^{61}$ groups include methyl, hydroxymethyl, ethyl, hydroxyethyl, propyl, isopropyl, n-butyl, sec-butyl, n-pentyl, n-hexyl, methoxy, methoxymethoxy, ethoxy and tert-butoxy.

Next, the adhesive groups represented by $R^{31}$ and $R^{49}$ are selected from a variety of such groups, preferably from among the groups of the following formulae.

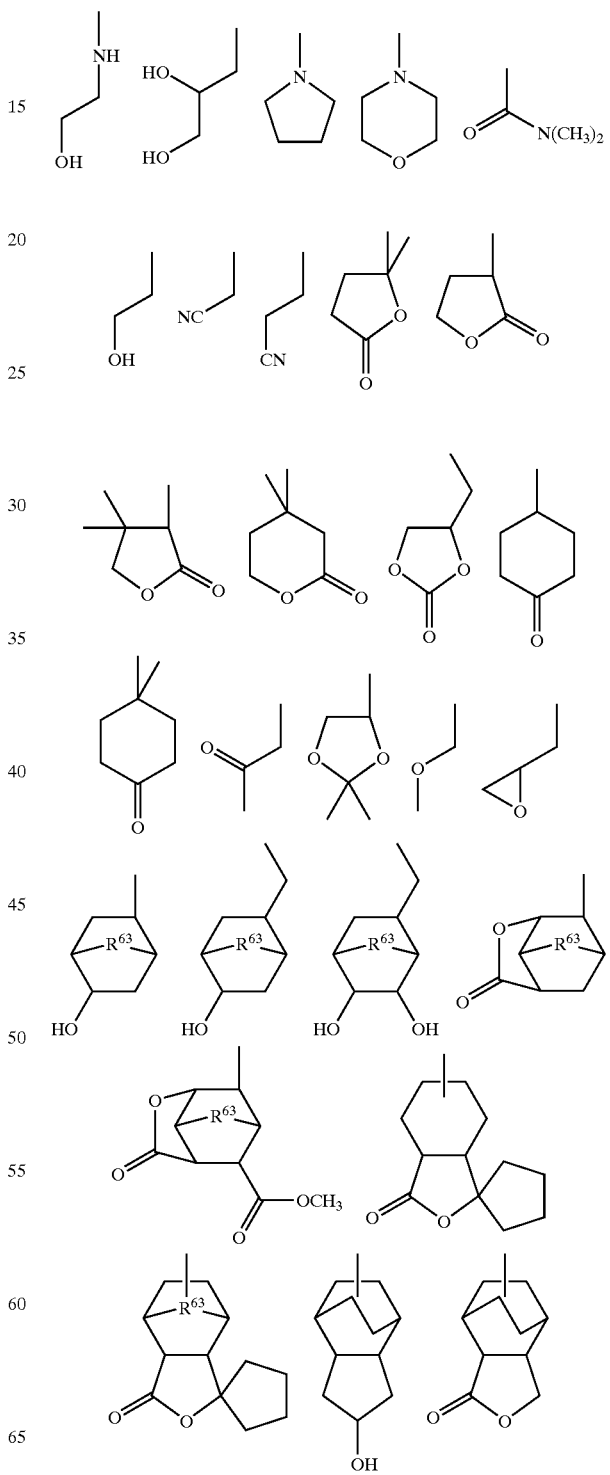

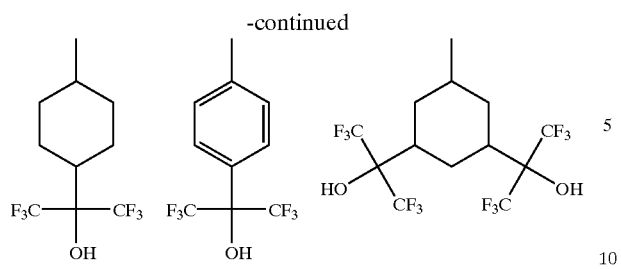

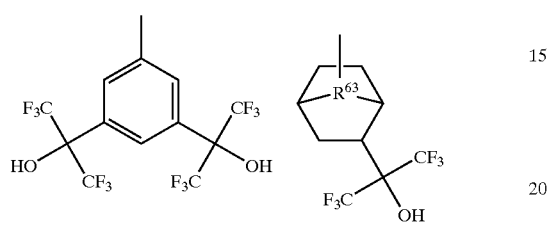

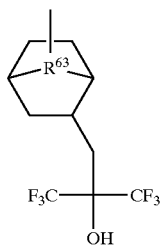

Herein, $R^{63}$ is a methylene group, oxygen atom or sulfur atom.

In the polymers of the invention, units of at least one type selected from the recurring units of formulae (5), (5a), (5b), (6), (6a), (6b), and (7), shown below, may be incorporated in addition to the above polymer units of formulae (2), (2a), (2b), (2'), (4a) and (4b) in order to improve the dissolution contrast, substrate adhesion and dry etching resistance of the resist.

(5)

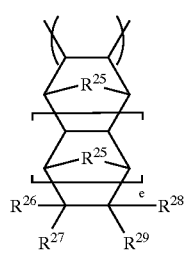

(5a)

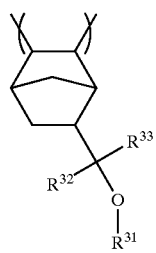

(5b)

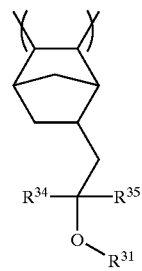

(6)

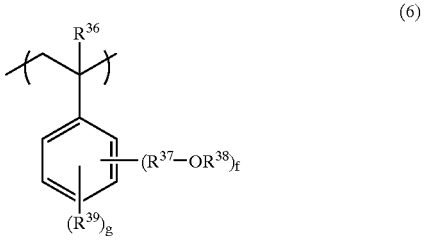

(6a)

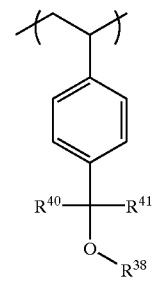

(6b)

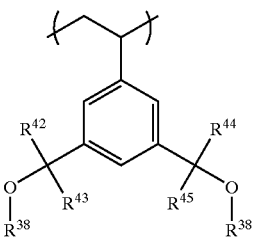

(7)

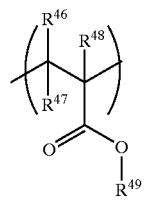

Herein $R^{25}$ is a methylene group, oxygen atom, sulfur atom or $SO_2$. $R^{26}$ to $R^{29}$ each are a hydrogen atom, a fluorine atom, $-R^{30}-OR^{31}$, $-R^{30}-CO_2R^{31}$ or a straight, branched or cyclic alkyl or fluorinated alkyl group of 1 to 20 carbon atoms, and at least one of $R^{26}$ to $R^{29}$ should contain $-R^{30}-OR^{31}$ or $-R^{30}-CO_2R^{31}$. $R^{30}$ is a valence bond or a straight, branched or cyclic alkylene or fluorinated alkylene group of 1 to 20 carbon atoms. $R^{31}$ is a hydrogen atom, an acid labile group, an adhesive group or a straight, branched or cyclic fluorinated alkyl group of 1 to 20 carbon atoms which may contain a hydrophilic group such as hydroxyl.

$R^{32}$ to $R^{35}$ each are a hydrogen atom, a fluorine atom or an alkyl or fluorinated alkyl group of 1 to 4 carbon atoms.

At least either one of $R^{32}$ and $R^{33}$ contains at least one fluorine atom, and at least either one of $R^{34}$ and $R^{35}$ contains at least one fluorine atom.

$R^{36}$ is a hydrogen atom, a fluorine atom or a straight, branched or cyclic alkyl or fluorinated alkyl group of 1 to 20 carbon atoms. $R^{37}$ is a valence bond or a straight, branched or cyclic alkylene or fluorinated alkylene group of 1 to 20 carbon atoms. $R^{38}$ is a hydrogen atom or acid labile group. $R^{39}$ is a fluorine atom or a straight, branched or cyclic fluorinated alkyl group of 1 to 20 carbon atoms.

$R^{40}$ to $R^{45}$ each are a hydrogen atom, fluorine atom or an alkyl or fluorinated alkyl group of 1 to 4 carbon atoms. At least either one of $R^{40}$ and $R^{41}$ contains at least one fluorine atom, at least either one of $R^{42}$ and $R^{43}$ contains at least one fluorine atom, and at least either one of $R^{44}$ and $R^{45}$ contains at least one fluorine atom.

$R^{46}$ to $R^{48}$ each are a hydrogen atom, fluorine atom or a straight, branched or cyclic alkyl or fluorinated alkyl group of 1 to 20 carbon atoms. $R^{49}$ is a hydrogen atom, an acid labile group, an adhesive group or a straight, branched or cyclic fluorinated alkyl group of 1 to 20 carbon atoms which may contain a hydrophilic group such as hydroxyl.

The subscript e is 0 or 1, f is 1 or 2, and g is an integer of 0 to 4, satisfying $1 \leq f+g \leq 5$.

Illustrative examples of the groups of formulae (2), (2a), (2b), (2'), (4a) and (4b) are given below, though not limited thereto.

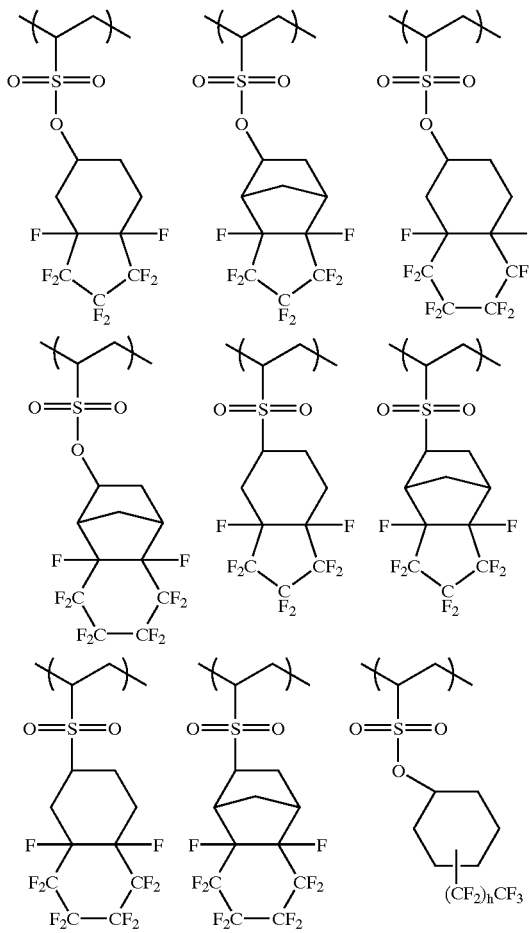

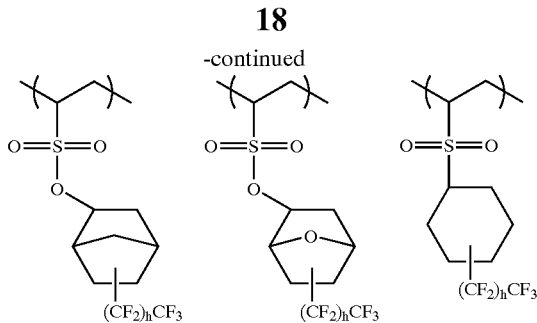

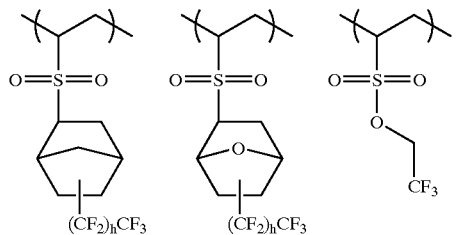

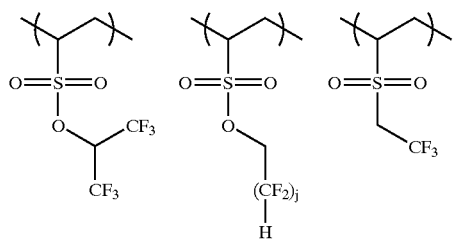

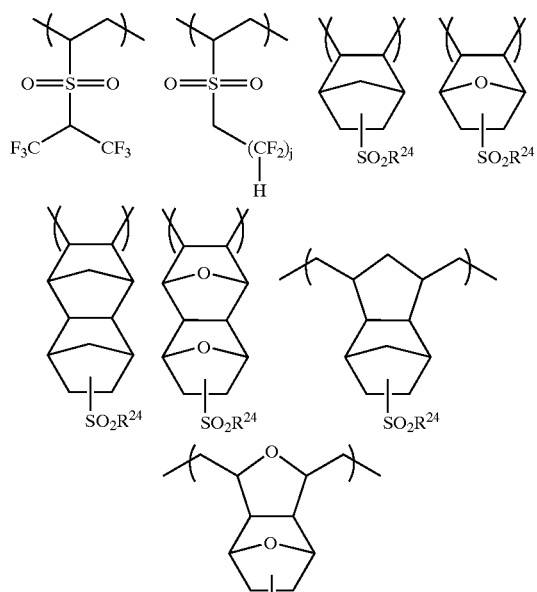

Herein $R^{24}$ and h are as defined above, and j is an integer of 1 to 6.

Illustrative examples of the units of formulae (5), (5a) and (5b) are given below, though not limited thereto.

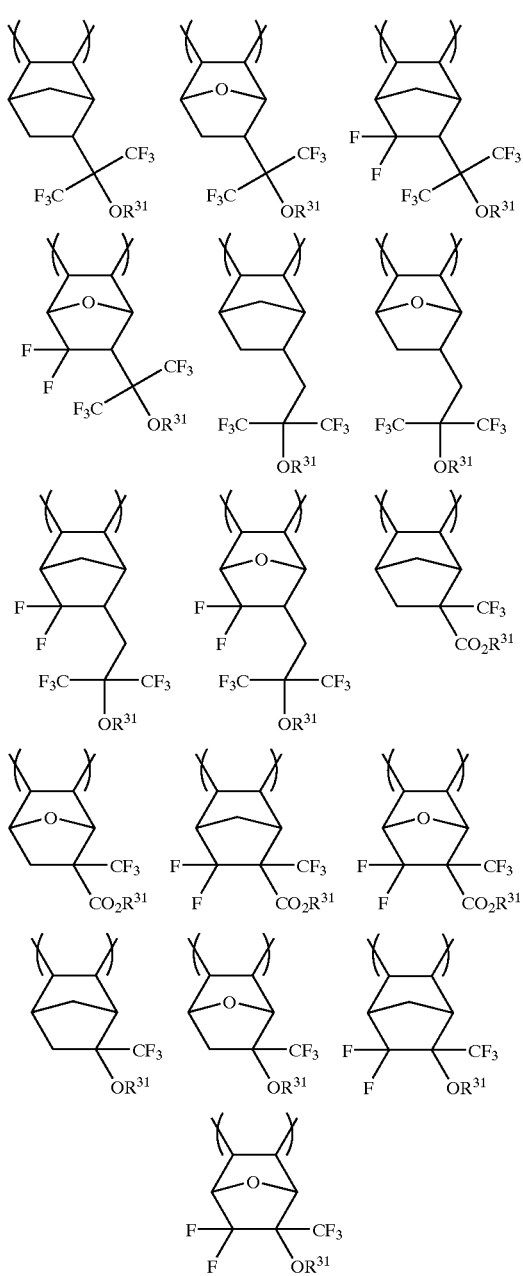

Herein $R^{31}$ is as defined above.

Illustrative examples of the units of formulae (6), (6a) and (6b) are given below, though not limited thereto.

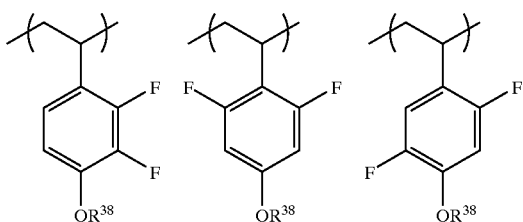

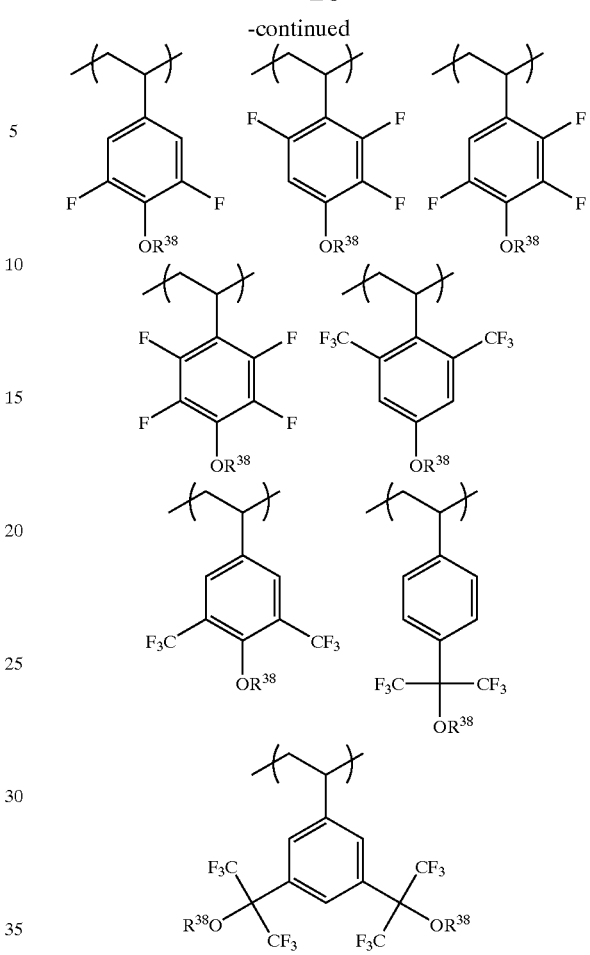

Herein $R^{38}$ is as defined above.

Besides, units as shown below may be incorporated in the inventive polymers for the purpose of improving substrate adhesion and transparency.

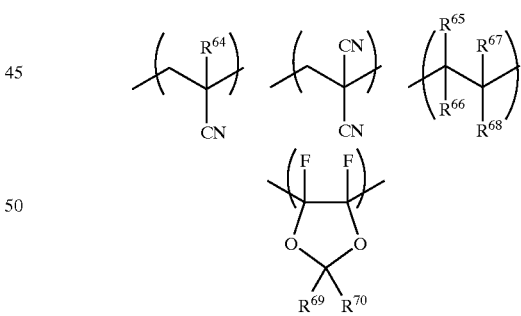

Herein, $R^{64}$ to $R^{68}$ each are hydrogen, fluorine or a fluorinated alkyl group of 1 to 4 carbon atoms, and at least one of $R^{65}$ to $R^{68}$ contains at least one fluorine atom. $R^{69}$ and $R^{70}$ each are hydrogen, methyl or trifluoromethyl.

In the inventive polymers wherein U2 represents units of formulae (2), (2a) and (2b), U3 represents units of formula (2'), U4 represents units of formulae (4a) and (4b), U5 represents units of formulae (5), (5a) and (5b), U6 represents units of formulae (6), (6a) and (6b), U7 represents units of formula (7), and U8 represents adhesive and transparent units other than the foregoing, and U2 (or U3 or U4)+U5+ U6+U7+U8=1, U's are preferably in the range:

$0 < U2 \leq 0.6$, more preferably $0.1 \leq U2 \leq 0.4$,
$0 < U3 \leq 0.6$, more preferably $0.1 \leq U3 \leq 0.4$,
$0 < U4 \leq 0.6$, more preferably $0.1 \leq U4 \leq 0.4$,
$0 \leq U5 \leq 0.6$, more preferably $0 \leq U5 \leq 0.4$,
$0 \leq U6 \leq 0.6$, more preferably $0 \leq U6 \leq 0.4$,
$0 \leq U7 \leq 0.7$, more preferably $0 \leq U7 \leq 0.5$, and
$0 \leq U8 \leq 0.4$, more preferably $0 \leq U8 \leq 0.2$.

The polymers of the invention are generally synthesized by dissolving monomers of formula (1), (1a) or (1b) or the like corresponding to the respective units of formula (2), (2a), (2b), (2'), (4a), (4b), (5), (5a), (5b), (6), (6a), (6b) or (7) and optionally, an adhesion-improving monomer, a transparency-improving monomer and the like in a solvent, adding a catalyst thereto, and effecting polymerization reaction while heating or cooling the system if necessary. The polymerization reaction depends on the type of initiator or catalyst, trigger means (including light, heat, radiation and plasma), and polymerization conditions (including temperature, pressure, concentration, solvent, and additives). Commonly used for preparation of the polymers of the invention are radical polymerization of triggering polymerization with initiators such as 2,2'-azobisisobutyronitrile (AIBN) or the like, and ion (anion) polymerization using catalysts such as alkyl lithium. These polymerization steps may be carried out in their conventional manner.

The radical polymerization initiator used herein is not critical. Exemplary initiators include azo compounds such as AIBN, 2,2'-azobis(4-methoxy-2,4-dimethylvaleronitrile), 2,2'-azobis(2,4-dimethylvaleronitrile), and 2,2'-azobis(2,4,4-trimethylpentane); peroxide compounds such as tert-butyl peroxypivalate, lauroyl peroxide, benzoyl peroxide and tert-butyl peroxylaurate; water-soluble initiators, for example, persulfate salts such as potassium persulfate; and redox combinations of potassium persulfate or peroxides such as hydrogen peroxide with reducing agents such as sodium sulfite. The amount of the polymerization initiator used is determined as appropriate in accordance with such factors as the identity of initiator and polymerization conditions, although the amount is often in the range of about 0.001 to 5% by weight, especially about 0.01 to 2% by weight based on the total weight of monomers to be polymerized.

For the polymerization reaction, a solvent may be used. The polymerization solvent used herein is preferably one which does not interfere with the polymerization reaction. Typical solvents include ester solvents such as ethyl acetate and n-butyl acetate, ketone solvents such as acetone, methyl ethyl ketone and methyl isobutyl ketone, aliphatic or aromatic hydrocarbon solvents such as toluene, xylene and cyclohexane, alcohol solvents such as isopropyl alcohol and ethylene glycol monomethyl ether, and ether solvents such as diethyl ether, dioxane, and tetrahydrofuran. These solvents may be used alone or in admixture of two or more. Further, any of well-known molecular weight modifiers such as dodecylmercaptan may be used in the polymerization system.

The temperature of polymerization reaction varies in accordance with the identity of polymerization initiator and the boiling point of the solvent although it is often preferably in the range of about 20 to 200° C., and especially about 50 to 140° C. Any desired reactor or vessel may be used for the polymerization reaction.

From the solution or dispersion of the polymer thus obtained, the organic solvent or water serving as the reaction medium is removed by any of well-known techniques. Suitable techniques include, for example, re-precipitation followed by filtration, and heat distillation under vacuum.

Desirably the polymer has a weight average molecular weight of about 1,000 to about 500,000, and especially about 2,000 to about 100,000.

The polymer of the invention can be used as a base resin in resist compositions, specifically chemical amplification type resist compositions, and especially chemical amplification type positive working resist compositions. It is understood that the polymer of the invention may be admixed with another polymer for the purpose of altering the dynamic properties, thermal properties, alkali solubility and other physical properties of polymer film. The type of the other polymer which can be admixed is not critical. Any of polymers known to be useful in resist use may be admixed in any desired proportion.

In the practice of the invention, the sulfonate compounds of the formulae (1), (1a) and (1b) can be prepared by the following processes, although their preparation is not limited thereto.

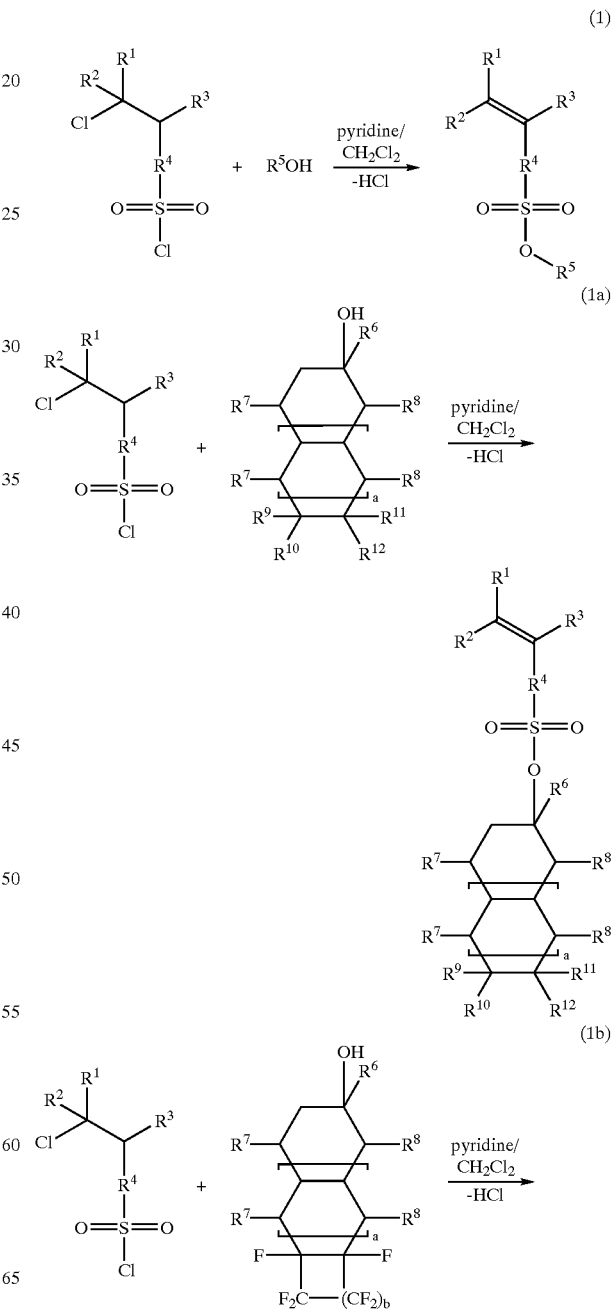

-continued

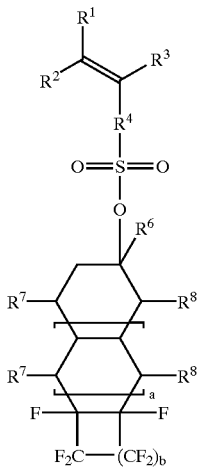

Herein R$^1$ to R$^{12}$, a and b are as defined above.

The reaction readily takes place under well-known conditions. Preferably, the alcohol reactant and a base such as pyridine are sequentially or simultaneously added to a solvent such as dichloromethane, and the sulfonic acid chloride is added dropwise under ice cooling. The salt thus formed is separated, and the product is purified by distillation or silica gel column chromatography, thereby isolating the end compound.

Resist Composition

As long as the polymer of the invention is used as a base resin, the resist composition of the invention may be prepared using well-known components. In a preferred embodiment, the chemically amplified positive resist composition is defined as comprising (A) the above-defined polymer as a base resin, (B) an organic solvent, and (C) a photoacid generator. In the resist composition, there may be further formulated (D) a basic compound and/or (E) a dissolution inhibitor.

Component (B)

The organic solvent used as component (B) in the invention may be any organic solvent in which the base resin, photoacid generator, and other components are soluble. Illustrative, non-limiting, examples of the organic solvent include ketones such as cyclohexanone and methyl-2-n-amylketone; alcohols such as 3-methoxybutanol, 3-methyl-3-methoxybutanol, 1-methoxy-2-propanol, and 1-ethoxy-2-propanol; ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether; esters such as propylene glycol monomethyl ether acetate, propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, and propylene glycol mono-tert-butyl ether acetate; and lactones such as γ-butyrolactone.

Also useful are fluorinated organic solvents. Illustrative, non-limiting examples include 2-fluoroanisole, 3-fluoroanisole, 4-fluoroanisole, 2,3-difluoroanisole, 2,4-difluoroanisole, 2,5-difluoroanisole, 5,8-difluoro-1,4-benzodioxane, 2,3-difluorobenzyl alcohol, 1,3-difluoro-2-propanol, 2',4'-difluoropropiophenone, 2,4-difluorotoluene, trifluoroacetaldehyde ethyl hemiacetal, trifluoroacetamide, trifluoroethanol, 2,2,2-trifluorobutyrate, ethylheptafluoroethanol, ethyl heptafluorobutylacetate, ethyl hexafluoroglutarylmethyl, ethyl 3-hydroxy-4,4,4-trifluoroacetoacetate, ethyl pentafluoropropynylacetate, ethyl perfluorooctanoate, ethyl 4,4,4-trifluoroacetoacetate, ethyl 4,4,4-trifluorobutyrate, ethyl 4,4,4-trifluorocrotonate, ethyl trifluoropyruvate, sec-ethyl trifluoroacetate, fluorocyclohexane, 2,2,3,3,4,4,4-heptafluoro-1-butanol, 1,1,1,2,2,3,3-heptafluoro-7,7-dimethyl-4,6-octanedione, 1,1,1,3,5,5,5-heptafluoropentane-2,4-dione, 3,3,4,4,5,5,5-heptafluoro-2-pentanol, 3,3,4,4,5,5,5-heptafluoro-2-pentanone, isopropyl 4,4,4-trifluoroacetoacetate, methyl perfluorodecanoate, methyl perfluoro(2-methyl-3-oxahexanoate), methyl perfluorononanoate, methyl perfluorooctanoate, methyl 2,3,3,3-tetrafluoropropionate, methyl trifluoroacetoacetate, 1,1,1,2,2,6,6,6-octafluoro-2,4-hexanedione, 2,2,3,3,4,4,5,5-octafluoro-1-pentanol, 1H,1H,2H,2H-perfluoro-1-decanol, perfluoro-2,5-dimethyl-3,6-dioxane anionic acid methyl ester, 2H-perfluoro-5-methyl-3,6-dioxanonane, 1H,1H,2H,3H,3H-perfluorononane-1,2-diol, 1H,1H,9H-perfluoro-1-nonanol, 1H,1H-perfluorooctanol, 1H,1H,2H,2H-perfluorooctanol, 2H-perfluoro-5,8,11,14-tetramethyl-3,6,9,12,15-pentaoxaoctadecane, perfluorotributylamine, perfluorotrihexylamine, perfluoro-2,5,8-trimethyl-3,6,9,12,15-pentaoxaoctadecane, methyl perfluoro-2,5,8-trimethyl-3,6,9-trioxadodecanoate, perfluorotripentylamine, perfluorotriisopropylamine, 1H,1H,2H,3H,3H-perfluoroundecane-1,2-diol, trifluorobutanol, 1,1,1-trifluoro-5-methyl-2,4-hexanedione, 1,1,1-trifluoro-2-propanol, 3,3,3-trifluoro-1-propanol, 1,1,1-trifluoro-2-propyl acetate, perfluorobutyltetrahydrofuran, perfluorodecalin, perfluoro(1,2-dimethylcyclohexane), perfluoro(1,3-dimethylcyclohexane), propylene glycol trifluoromethyl ether acetate, propylene glycol methyl ether trifluoromethyl acetate, butyl trifluoromethylacetate, methyl 3-trifluoromethoxypropionate, perfluorocyclohexanone, propylene glycol trifluoromethyl ether, butyl trifluoroacetate, and 1,1,1-trifluoro-5,5-dimethyl-2,4-hexanedione.

These solvents may be used alone or in combinations of two or more thereof. Of the above organic solvents, preferred are diethylene glycol dimethyl ether and 1-ethoxy-2-propanol, in which the photoacid generator is most soluble, and propylene glycol monomethyl ether acetate which is safe, and mixtures thereof.

The solvent is preferably used in an amount of about 300 to 10,000 parts by weight, more preferably about 500 to 5,000 parts by weight per 100 parts by weight of the base resin.

Component (C)

The photoacid generator is a compound capable of generating an acid upon exposure to high energy radiation or electron beams and includes the following:
(i) onium salts of the formula (P1a-1), (P1a-2) or (P1b),
(ii) diazomethane derivatives of the formula (P2),
(iii) glyoxime derivatives of the formula (P3),
(iv) bissulfone derivatives of the formula (P4),
(v) sulfonic acid esters of N-hydroxyimide compounds of the formula (P5),
(vi) β-ketosulfonic acid derivatives,
(vii) disulfone derivatives,
(viii) nitrobenzylsulfonate derivatives, and
(ix) sulfonate derivatives.

These photoacid generators are described in detail.
(i) Onium Salts of Formula (P1a-1), (P1a-2) or (P1b):

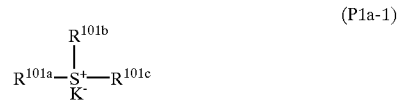

(P1a-1)

Herein, $R^{101a}$, $R^{101b}$, and $R^{101c}$ independently represent straight, branched or cyclic alkyl, alkenyl, oxoalkyl or oxoalkenyl groups of 1 to 12 carbon atoms, aryl groups of 6 to 20 carbon atoms, or aralkyl or aryloxoalkyl groups of 7 to 12 carbon atoms, wherein some or all of the hydrogen atoms may be replaced by alkoxy or other groups. Also, $R^{101b}$ and $R^{101c}$, taken together, may form a ring. $R^{101b}$ and $R^{101c}$ each are alkylene groups of 1 to 6 carbon atoms when they form a ring. $K^-$ is a non-nucleophilic counter ion.

$R^{101a}$, $R^{101b}$, and $R^{101c}$ may be the same or different and are illustrated below. Exemplary alkyl groups include methyl, ethyl, propyl, isopropyl, n-butyl, sec-butyl, tert-butyl, pentyl, hexyl, heptyl, octyl, cyclopentyl, cyclohexyl, cycloheptyl, cyclopropylmethyl, 4-methylcyclohexyl, cyclohexylmethyl, norbornyl, and adamantyl. Exemplary alkenyl groups include vinyl, allyl, propenyl, butenyl, hexenyl, and cyclohexenyl. Exemplary oxoalkyl groups include 2-oxocyclopentyl and 2-oxocyclohexyl as well as 2-oxopropyl, 2-cyclopentyl-2-oxoethyl, 2-cyclohexyl-2-oxoethyl, and 2-(4-methylcyclohexyl)-2-oxoethyl. Exemplary aryl groups include phenyl and naphthyl; alkoxyphenyl groups such as p-methoxyphenyl, m-methoxyphenyl, o-methoxyphenyl, ethoxyphenyl, p-tert-butoxyphenyl, and m-tert-butoxyphenyl; alkylphenyl groups such as 2-methylphenyl, 3-methylphenyl, 4-methylphenyl, ethylphenyl, 4-tert-butylphenyl, 4-butylphenyl, and dimethylphenyl; alkylnaphthyl groups such as methylnaphthyl and ethylnaphthyl; alkoxynaphthyl groups such as methoxynaphthyl and ethoxynaphthyl; dialkylnaphthyl groups such as dimethylnaphthyl and diethylnaphthyl; and dialkoxynaphthyl groups such as dimethoxynaphthyl and diethoxynaphthyl. Exemplary aralkyl groups include benzyl, phenylethyl, and phenethyl. Exemplary aryloxoalkyl groups are 2-aryl-2-oxoethyl groups such as 2-phenyl-2-oxoethyl, 2-(1-naphthyl)-2-oxoethyl, and 2-(2-naphthyl)-2-oxoethyl. Examples of the non-nucleophilic counter ion represented by $K^-$ include halide ions such as chloride and bromide ions, fluoroalkylsulfonate ions such as triflate, 1,1,1-trifluoroethanesulfonate, and nonafluorobutanesulfonate, arylsulfonate ions such as tosylate, benzenesulfonate, 4-fluorobenzenesulfonate, and 1,2,3,4,5-pentafluorobenzenesulfonate, and alkylsulfonate ions such as mesylate and butanesulfonate.

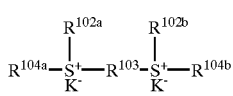

Herein, $R^{102a}$ and $R^{102b}$ independently represent straight, branched or cyclic alkyl groups of 1 to 8 carbon atoms. $R^{103}$ represents a straight, branched or cyclic alkylene group of 1 to 10 carbon atoms. $R^{104a}$ and $R^{104b}$ independently represent 2-oxoalkyl groups of 3 to 7 carbon atoms. $K^-$ is a non-nucleophilic counter ion.

Illustrative of the groups represented by $R^{102a}$ and $R^{102b}$ are methyl, ethyl, propyl, isopropyl, n-butyl, sec-butyl, tert-butyl, pentyl, hexyl, heptyl, octyl, cyclopentyl, cyclohexyl, cyclopropylmethyl, 4-methylcyclohexyl, and cyclohexylmethyl. Illustrative of the groups represented by $R^{103}$ are methylene, ethylene, propylene, butylene, pentylene, hexylene, heptylene, octylene, nonylene, 1,4-cyclohexylene, 1,2-cyclohexylene, 1,3-cyclopentylene, 1,4-cyclooctylene, and 1,4-cyclohexanedimethylene. Illustrative of the groups represented by $R^{104a}$ and $R^{104b}$ are 2-oxopropyl, 2-oxocyclopentyl, 2-oxocyclohexyl, and 2-oxocycloheptyl. Illustrative examples of the counter ion represented by $K^-$ are the same as exemplified for formulae (P1a-1) and (P1a-2).

(ii) Diazomethane Derivatives of Formula (P2)

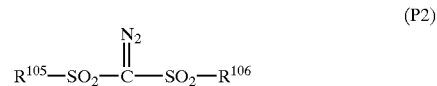

Herein, $R^{105}$ and $R^{106}$ independently represent straight, branched or cyclic alkyl or halogenated alkyl groups of 1 to 12 carbon atoms, aryl or halogenated aryl groups of 6 to 20 carbon atoms, or aralkyl groups of 7 to 12 carbon atoms.

Of the groups represented by $R^{105}$ and $R^{106}$, exemplary alkyl groups include methyl, ethyl, propyl, isopropyl, n-butyl, sec-butyl, tert-butyl, pentyl, hexyl, heptyl, octyl, amyl, cyclopentyl, cyclohexyl, cycloheptyl, norbornyl, and adamantyl. Exemplary halogenated alkyl groups include trifluoromethyl, 1,1,1-trifluoroethyl, 1,1,1-trichloroethyl, and nonafluorobutyl. Exemplary aryl groups include phenyl; alkoxyphenyl groups such as p-methoxyphenyl, m-methoxyphenyl, o-methoxyphenyl, ethoxyphenyl, p-tert-butoxyphenyl, and m-tert-butoxyphenyl; and alkylphenyl groups such as 2-methylphenyl, 3-methylphenyl, 4-methylphenyl, ethylphenyl, 4-tert-butylphenyl, 4-butylphenyl, and dimethylphenyl. Exemplary halogenated aryl groups include fluorophenyl, chlorophenyl, and 1,2,3,4,5-pentafluorophenyl. Exemplary aralkyl groups include benzyl and phenethyl.

(iii) Glyoxime Derivatives of Formula (P3)

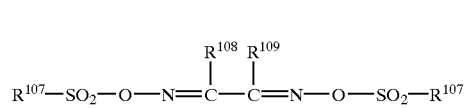

Herein, $R^{107}$, $R^{108}$, and $R^{109}$ independently represent straight, branched or cyclic alkyl or halogenated alkyl groups of 1 to 12 carbon atoms, aryl or halogenated aryl groups of 6 to 20 carbon atoms, or aralkyl groups of 7 to 12 carbon atoms. Also, $R^{108}$ and $R^{109}$, taken together, may form a ring. $R^{108}$ and $R^{109}$ each are straight or branched alkylene groups of 1 to 6 carbon atoms when they form a ring.

Illustrative examples of the alkyl, halogenated alkyl, aryl, halogenated aryl, and aralkyl groups represented by $R^{107}$, $R^{108}$, and $R^{109}$ are the same as exemplified for $R^{105}$ and $R^{106}$. Examples of the alkylene groups represented by $R^{108}$ and $R^{109}$ include methylene, ethylene, propylene, butylene, and hexylene.

(iv) Bissulfone Derivatives of Formula (P4)

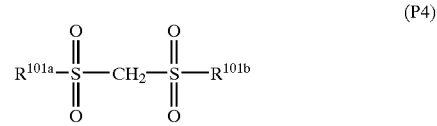

Herein, $R^{101a}$ and $R^{101b}$ are as defined above.

(v) Sulfonic Acid Esters of N-hydroxyimide Compounds of Formula (P5)

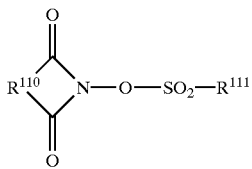
(P5)

Herein, $R^{110}$ is an arylene group of 6 to 10 carbon atoms, alkylene group of 1 to 6 carbon atoms, or alkenylene group of 2 to 6 carbon atoms wherein some or all of the hydrogen atoms may be replaced by straight or branched alkyl or alkoxy groups of 1 to 4 carbon atoms, nitro, acetyl, or phenyl groups. $R^{111}$ is a straight, branched or cyclic alkyl group of 1 to 8 carbon atoms, alkenyl, alkoxyalkyl, phenyl or naphthyl group wherein some or all of the hydrogen atoms may be replaced by alkyl or alkoxy groups of 1 to 4 carbon atoms, phenyl groups (which may have substituted thereon an alkyl or alkoxy of 1 to 4 carbon atoms, nitro, or acetyl group), hetero-aromatic groups of 3 to 5 carbon atoms, or chlorine or fluorine atoms.

Of the groups represented by $R^{110}$, exemplary arylene groups include 1,2-phenylene and 1,8-naphthylene; exemplary alkylene groups include methylene, ethylene, trimethylene, tetramethylene, phenylethylene, and norbornane-2,3-diyl; and exemplary alkenylene groups include 1,2-vinylene, 1-phenyl-1,2-vinylene, and 5-norbornene-2,3-diyl. Of the groups represented by $R^{111}$, exemplary alkyl groups are as exemplified for $R^{101a}$ to $R^{101c}$; exemplary alkenyl groups include vinyl, 1-propenyl, allyl, 1-butenyl, 3-butenyl, isoprenyl, 1-pentenyl, 3-pentenyl, 4-pentenyl, dimethylallyl, 1-hexenyl, 3-hexenyl, 5-hexenyl, 1-heptenyl, 3-heptenyl, 6-heptenyl, and 7-octenyl; and exemplary alkoxyalkyl groups include methoxymethyl, ethoxymethyl, propoxymethyl, butoxymethyl, pentyloxymethyl, hexyloxymethyl, heptyloxymethyl, methoxyethyl, ethoxyethyl, propoxyethyl, butoxyethyl, pentyloxyethyl, hexyloxyethyl, methoxypropyl, ethoxypropyl, propoxypropyl, butoxypropyl, methoxybutyl, ethoxybutyl, propoxybutyl, methoxypentyl, ethoxypentyl, methoxyhexyl, and methoxyheptyl.

Of the substituents on these groups, the alkyl groups of 1 to 4 carbon atoms include methyl, ethyl, propyl, isopropyl, n-butyl, isobutyl and tert-butyl; the alkoxy groups of 1 to 4 carbon atoms include methoxy, ethoxy, propoxy, isopropoxy, n-butoxy, isobutoxy, and tert-butoxy; the phenyl groups which may have substituted thereon an alkyl or alkoxy of 1 to 4 carbon atoms, nitro, or acetyl group include phenyl, tolyl, p-tert-butoxyphenyl, p-acetylphenyl and p-nitrophenyl; the hetero-aromatic groups of 3 to 5 carbon atoms include pyridyl and furyl.

Illustrative examples of the photoacid generator include: onium salts such as diphenyliodonium trifluoromethanesulfonate, (p-tert-butoxyphenyl)phenyliodonium trifluoromethanesulfonate, diphenyliodonium p-toluenesulfonate, (p-tert-butoxyphenyl)phenyliodonium p-toluenesulfonate, triphenylsulfonium trifluoromethanesulfonate, (p-tert-butoxyphenyl)diphenylsulfonium trifluoromethanesulfonate, bis(p-tert-butoxyphenyl)phenylsulfonium trifluoromethanesulfonate, tris(p-tert-butoxyphenyl)sulfonium trifluoromethanesulfonate, triphenylsulfonium p-toluenesulfonate, (p-tert-butoxyphenyl)diphenylsulfonium p-toluenesulfonate, bis(p-tert-butoxyphenyl)phenylsulfonium p-toluenesulfonate, tris(p-tert-butoxyphenyl)sulfonium p-toluenesulfonate, triphenylsulfonium nonafluorobutanesulfonate, triphenylsulfonium butanesulfonate, trimethylsulfonium trifluoromethanesulfonate, trimethylsulfonium p-toluenesulfonate, cyclohexylmethyl(2-oxocyclohexyl)sulfonium trifluoromethanesulfonate, cyclohexylmethyl(2-oxocyclohexyl)sulfonium p-toluenesulfonate, dimethylphenylsulfonium trifluoromethanesulfonate, dimethylphenylsulfonium p-toluenesulfonate, dicyclohexylphenylsulfonium trifluoromethanesulfonate, dicyclohexylphenylsulfonium p-toluenesulfonate, trinaphthylsulfonium trifluoromethanesulfonate, cyclohexylmethyl(2-oxocyclohexyl)sulfonium trifluoromethanesulfonate, (2-norbornyl)methyl(2-oxocyclohexyl)sulfonium trifluoromethanesulfonate, ethylenebis[methyl(2-oxocyclopentyl)sulfonium trifluoromethanesulfonate], and 1,2'-naphthylcarbonylmethyltetrahydrothiophenium triflate;

diazomethane derivatives such as bis(benzenesulfonyl)diazomethane, bis(p-toluenesulfonyl)diazomethane, bis(xylenesulfonyl)diazomethane, bis(cyclohexylsulfonyl)diazomethane, bis(cyclopentylsulfonyl)diazomethane, bis(n-butylsulfonyl)diazomethane, bis(isobutylsulfonyl)diazomethane, bis(sec-butylsulfonyl)diazomethane, bis(n-propylsulfonyl)diazomethane, bis(isopropylsulfonyl)diazomethane, bis(tert-butylsulfonyl)diazomethane, bis(n-amylsulfonyl)diazomethane, bis(isoamylsulfonyl)diazomethane, bis(sec-amylsulfonyl)diazomethane, bis(tert-amylsulfonyl)diazomethane, 1-cyclohexylsulfonyl-1-(tert-butylsulfonyl)diazomethane, 1-cyclohexylsulfonyl-1-(tert-amylsulfonyl)diazomethane, and 1-tert-amylsulfonyl-1-(tert-butylsulfonyl)diazomethane;

glyoxime derivatives such as bis-O-(p-toluenesulfonyl)-α-dimethylglyoxime, bis-O-(p-toluenesulfonyl)-α-diphenylglyoxime, bis-O-(p-toluenesulfonyl)-α-dicyclohexylglyoxime, bis-O-(p-toluenesulfonyl)-2,3-pentanedioneglyoxime, bis-O-(p-toluenesulfonyl)-2-methyl-3,4-pentanedioneglyoxime, bis-O-(n-butanesulfonyl)-α-dimethylglyoxime, bis-O-(n-butanesulfonyl)-α-diphenylglyoxime, bis-O-(n-butanesulfonyl)-α-dicyclohexylglyoxime, bis-O-(n-butanesulfonyl)-2,3-pentanedioneglyoxime, bis-O-(n-butanesulfonyl)-2-methyl-3,4-pentanedioneglyoxime, bis-O-(methanesulfonyl)-α-dimethylglyoxime, bis-O-(trifluoromethanesulfonyl)-α-dimethylglyoxime, bis-O-(1,1,1-trifluoroethanesulfonyl)-α-dimethylglyoxime, bis-O-(tert-butanesulfonyl)-α-dimethylglyoxime, bis-O-(perfluorooctanesulfonyl)-α-dimethylglyoxime, bis-O-(cyclohexanesulfonyl)-α-dimethylglyoxime, bis-O-(benzenesulfonyl)-α-dimethylglyoxime, bis-O-(p-fluorobenzenesulfonyl)-α-dimethylglyoxime, bis-O-(p-tert-butylbenzenesulfonyl)-α-dimethylglyoxime, bis-O-(xylenesulfonyl)-α-dimethylglyoxime, and bis-O-(camphorsulfonyl)-α-dimethylglyoxime;

bissulfone derivatives such as bisnaphthylsulfonylmethane, bistrifluoromethylsulfonylmethane, bismethylsulfonylmethane, bisethylsulfonylmethane, bispropylsulfonylmethane, bisisopropylsulfonylmethane, bis-p-toluenesulfonylmethane, and bisbenzenesulfonylmethane;

β-ketosulfone derivatives such as 2-cyclohexylcarbonyl-2-(p-toluenesulfonyl)propane and 2-isopropylcarbonyl-2-(p-toluenesulfonyl)propane;

nitrobenzyl sulfonate derivatives such as 2,6-dinitrobenzyl p-toluenesulfonate and 2,4-dinitrobenzyl p-toluenesulfonate;

sulfonic acid ester derivatives such as 1,2,3-tris(methanesulfonyloxy)benzene, 1,2,3-tris(trifluoromethanesulfonyloxy)benzene, and 1,2,3-tris(p-toluenesulfonyloxy)benzene; and sulfonic acid esters of N-hydroxyimides such as N-hydroxysuccinimide methanesulfonate, N-hydroxysuccinimide trifluoromethanesulfonate, N-hydroxysuccinimide ethanesulfonate, N-hydroxysuccinimide 1-propanesulfonate, N-hydroxysuccinimide 2-propanesulfonate, N-hydroxysuccinimide 1-pentanesulfonate, N-hydroxysuccinimide 1-octanesulfonate, N-hydroxysuccinimide p-toluenesulfonate, N-hydroxysuccinimide p-methoxybenzenesulfonate, N-hydroxysuccinimide 2-chloroethanesulfonate, N-hydroxysuccinimide benzenesulfonate, N-hydroxysuccinimide 2,4,6-trimethylbenzenesulfonate, N-hydroxysuccinimide 1-naphthalenesulfonate, N-hydroxysuccinimide 2-naphthalenesulfonate, N-hydroxy-2-phenylsuccinimide methanesulfonate, N-hydroxymaleimide methanesulfonate, N-hydroxymaleimide ethanesulfonate, N-hydroxy-2-phenylmaleimide methanesulfonate, N-hydroxyglutarimide methanesulfonate, N-hydroxyglutarimide benzenesulfonate, N-hydroxyphthalimide methanesulfonate, N-hydroxyphthalimide benzenesulfonate, N-hydroxyphthalimide trifluoromethanesulfonate, N-hydroxyphthalimide p-toluenesulfonate, N-hydroxynaphthalimide methanesulfonate, N-hydroxynaphthalimide benzenesulfonate, N-hydroxy-5-norbornene-2,3-dicarboxyimide methanesulfonate, N-hydroxy-5-norbornene-2,3-dicarboxyimide trifluoromethanesulfonate, and N-hydroxy-5-norbornene-2,3-dicarboxyimide p-toluenesulfonate.

Preferred among these photoacid generators are onium salts such as triphenylsulfonium trifluoromethanesulfonate, (p-tert-butoxyphenyl)diphenylsulfonium trifluoromethanesulfonate, tris(p-tert-butoxyphenyl)sulfonium trifluoromethanesulfonate, triphenylsulfonium p-toluenesulfonate, (p-tert-butoxyphenyl)diphenylsulfonium p-toluenesulfonate, tris(p-tert-butoxyphenyl)sulfonium p-toluenesulfonate, trinaphthylsulfonium trifluoromethanesulfonate, cyclohexylmethyl(2-oxocyclohexyl)sulfonium trifluoromethanesulfonate, (2-norbornyl)methyl(2-oxocyclohexyl)sulfonium trifluoromethanesulfonate, and 1,2'-naphthylcarbonylmethyltetrahydrothiophenium triflate; diazomethane derivatives such as bis(benzenesulfonyl)diazomethane, bis(p-toluenesulfonyl)diazomethane, bis(cyclohexylsulfonyl)diazomethane, bis(n-butylsulfonyl)diazomethane, bis(isobutylsulfonyl)diazomethane, bis(sec-butylsulfonyl)diazomethane, bis(n-propylsulfonyl)diazomethane, bis(isopropylsulfonyl)diazomethane, and bis(tert-butylsulfonyl)diazomethane; glyoxime derivatives such as bis-O-(p-toluenesulfonyl)-α-dimethylglyoxime and bis-O-(n-butanesulfonyl)-α-dimethylglyoxime; bissulfone derivatives such as bisnaphthylsulfonylmethane; and sulfonic acid esters of N-hydroxyimide compounds such as N-hydroxysuccinimide methanesulfonate, N-hydroxysuccinimide trifluoromethanesulfonate, N-hydroxysuccinimide 1-propanesulfonate, N-hydroxysuccinimide 2-propanesulfonate, N-hydroxysuccinimide 1-pentanesulfonate, N-hydroxysuccinimide p-toluenesulfonate, N-hydroxynaphthalimide methanesulfonate, and N-hydroxynaphthalimide benzenesulfonate.

These photoacid generators may be used singly or in combinations of two or more thereof. Onium salts are effective for improving rectangularity, while diazomethane derivatives and glyoxime derivatives are effective for reducing standing waves. The combination of an onium salt with a diazomethane or a glyoxime derivative allows for fine adjustment of the profile.

The photoacid generator is added in an amount of 0.1 to 50 parts, and especially 0.5 to 40 parts by weight, per 100 parts by weight of the base resin (all parts are by weight, hereinafter). Less than 0.1 part of the photoacid generator may generate a less amount of acid upon exposure, sometimes leading to a poor sensitivity and resolution whereas more than 50 parts of the photoacid generator may adversely affect transparency and resolution.

Component (D)

The basic compound used as component (D) is preferably a compound capable of suppressing the rate of diffusion when the acid generated by the photoacid generator diffuses within the resist film. The inclusion of this type of basic compound holds down the rate of acid diffusion within the resist film, resulting in better resolution. In addition, it suppresses changes in sensitivity following exposure, thus reducing substrate and environment dependence, as well as improving the exposure latitude and the pattern profile.

Examples of suitable basic compounds include primary, secondary, and tertiary aliphatic amines, mixed amines, aromatic amines, heterocyclic amines, carboxyl group-bearing nitrogenous compounds, sulfonyl group-bearing nitrogenous compounds, hydroxyl group-bearing nitrogenous compounds, hydroxyphenyl group-bearing nitrogenous compounds, alcoholic nitrogenous compounds, amide derivatives, and imide derivatives.

Examples of suitable primary aliphatic amines include ammonia, methylamine, ethylamine, n-propylamine, isopropylamine, n-butylamine, iso-butylamine, sec-butylamine, tert-butylamine, pentylamine, tert-amylamine, cyclopentylamine, hexylamine, cyclohexylamine, heptylamine, octylamine, nonylamine, decylamine, dodecylamine, cetylamine, methylenediamine, ethylenediamine, and tetraethylenepentamine. Examples of suitable secondary aliphatic amines include dimethylamine, diethylamine, di-n-propylamine, di-iso-propylamine, di-n-butylamine, di-iso-butylamine, di-sec-butylamine, dipentylamine, dicyclopentylamine, dihexylamine, dicyclohexylamine, diheptylamine, dioctylamine, dinonylamine, didecylamine, didodecylamine, dicetylamine, N,N-dimethylmethylenediamine, N,N-dimethylethylenediamine, and N,N-dimethyltetraethylenepentamine. Examples of suitable tertiary aliphatic amines include trimethylamine, triethylamine, tri-n-propylamine, tri-iso-propylamine, tri-n-butylamine, tri-iso-butylamine, tri-sec-butylamine, tripentylamine, tricyclopentylamine, trihexylamine, tricyclohexylamine, triheptylamine, trioctylamine, trinonylamine, tridecylamine, tridodecylamine, tricetylamine, N,N,N',N'-tetramethylmethylenediamine, N,N,N',N'-tetramethylethylenediamine, and N,N,N',N'-tetramethyltetraethylenepentamine.

Examples of suitable mixed amines include dimethylethylamine, methylethylpropylamine, benzylamine, phenethylamine, and benzyldimethylamine. Examples of suitable aromatic amines include aniline derivatives (e.g., aniline, N-methylaniline, N-ethylaniline, N-propylaniline, N,N-dimethylaniline, 2-methylaniline, 3-methylaniline, 4-methylaniline, ethylaniline, propylaniline, trimethylaniline, 2-nitroaniline, 3-nitroaniline, 4-nitroaniline, 2,4-dinitroaniline, 2,6-dinitroaniline, 3,5-dinitroaniline, and N,N-dimethyltoluidine), diphenyl(p-tolyl)amine, methyldiphenylamine, triphenylamine, phenylenediamine, naphthylamine, and diaminonaphthalene. Examples of suitable heterocyclic amines include pyrrole derivatives (e.g., pyrrole, 2H-pyrrole, 1-methylpyrrole, 2,4-dimethylpyrrole, 2,5-dimethylpyrrole, and N-methylpyrrole), oxazole derivatives (e.g., oxazole and isooxazole), thiazole derivatives (e.g., thiazole and isothiazole), imidazole derivatives (e.g., imidazole, 4-methylimidazole, and 4-methyl-2-phenylimidazole), pyrazole derivatives, furazan derivatives, pyrroline derivatives (e.g., pyrroline and 2-methyl-1-pyrroline), pyrrolidine derivatives (e.g., pyrrolidine, N-methylpyrrolidine, pyrrolidinone, and N-methylpyrrolidone), imidazoline derivatives, imidazolidine derivatives, pyridine derivatives (e.g., pyridine, methylpyridine, ethylpyridine, propylpyridine, butylpyridine, 4-(1-butylpentyl)pyridine, dimethylpyridine, trimethylpyridine, triethylpyridine, phenylpyridine, 3-methyl-2-phenylpyridine, 4-tert-butylpyridine, diphenylpyridine, benzylpyridine, methoxypyridine, butoxypyridine, dimethoxypyridine, 1-methyl-2-pyridine, 4-pyrrolidinopyridine, 1-methyl-4-phenylpyridine, 2-(1-ethylpropyl)pyridine, aminopyridine, and dimethylaminopyridine), pyridazine derivatives, pyrimidine derivatives, pyrazine derivatives, pyrazoline derivatives, pyrazolidine derivatives, piperidine derivatives, piperazine derivatives, morpholine derivatives, indole derivatives, isoindole derivatives, 1H-indazole derivatives, indoline derivatives, quinoline derivatives (e.g., quinoline and 3-quinolinecarbonitrile), isoquinoline derivatives, cinnoline derivatives, quinazoline derivatives, quinoxaline derivatives, phthalazine derivatives, purine derivatives, pteridine derivatives, carbazole derivatives, phenanthridine derivatives, acridine derivatives, phenazine derivatives, 1,10-phenanthroline derivatives, adenine derivatives, adenosine derivatives, guanine derivatives, guanosine derivatives, uracil derivatives, and uridine derivatives.

Examples of suitable carboxyl group-bearing nitrogenous compounds include aminobenzoic acid, indolecarboxylic acid, and amino acid derivatives (e.g., nicotinic acid, alanine, alginine, aspartic acid, glutamic acid, glycine, histidine, isoleucine, glycylleucine, leucine, methionine, phenylalanine, threonine, lysine, 3-aminopyrazine-2-carboxylic acid, and methoxyalanine).

Examples of suitable sulfonyl group-bearing nitrogenous compounds include 3-pyridinesulfonic acid and pyridinium p-toluenesulfonate.

Examples of suitable hydroxyl group-bearing nitrogenous compounds, hydroxyphenyl group-bearing nitrogenous compounds, and alcoholic nitrogenous compounds include 2-hydroxypyridine, aminocresol, 2,4-quinolinediol, 3-indolemethanol hydrate, monoethanolamine, diethanolamine, triethanolamine, N-ethyldiethanolamine, N,N-diethylethanolamine, triisopropanolamine, 2,2'-iminodiethanol, 2-aminoethanol, 3-amino-1-propanol, 4-amino-1-butanol, 4-(2-hydroxyethyl)morpholine, 2-(2-hydroxyethyl)pyridine, 1-(2-hydroxyethyl)piperazine, 1-[2-(2-hydroxyethoxy)ethyl]piperazine, piperidine ethanol, 1-(2-hydroxyethyl)pyrrolidine, 1-(2-hydroxyethyl)-2-pyrrolidinone, 3-piperidino-1,2-propanediol, 3-pyrrolidino-1,2-propanediol, 8-hydroxyjulolidine, 3-quinuclidinol, 3-tropanol, 1-methyl-2-pyrrolidine ethanol, 1-aziridine ethanol, N-(2-hydroxyethyl)phthalimide, and N-(2-hydroxyethyl)isonicotinamide.

Examples of suitable amide derivatives include formamide, N-methylformamide, N,N-dimethylformamide, acetamide, N-methylacetamide, N,N-dimethylacetamide, propionamide, and benzamide. Suitable imide derivatives include phthalimide, succinimide, and maleimide.

In addition, basic compounds of the following general formula (B)-1 may also be included alone or in admixture.

In the formulas, n is 1, 2 or 3. The side chain X may be the same or different and is represented by the formula (X)-1, (X)-2 or (X)-3. The side chain Y may be the same or different and stands for hydrogen or a straight, branched or cyclic alkyl group of 1 to 20 carbon atoms which may contain an ether or hydroxyl group. Two or three X's may bond together to form a ring.

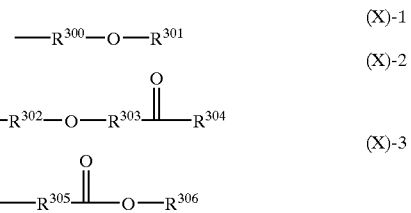

In the formulas, $R^{300}$, $R^{302}$ and $R^{305}$ are independently straight or branched alkylene groups of 1 to 4 carbon atoms; $R^{301}$ and $R^{304}$ are independently hydrogen, straight, branched or cyclic alkyl groups of 1 to 20 carbon atoms, which may contain at least one hydroxyl group, ether, ester or lactone ring; and $R^{303}$ is a single bond or a straight or branched alkylene group of 1 to 4 carbon atoms; and $R^{306}$ is a straight, branched or cyclic alkyl group of 1 to 20 carbon atoms, which may contain at least one hydroxyl group, ether, ester or lactone ring.

Illustrative, non-limiting examples of the compounds of formula (B)-1 include tris(2-methoxymethoxyethyl)amine, tris{2-(2-methoxyethoxy)ethyl}amine, tris{2-(2-methoxyethoxymethoxy)ethyl}amine, tris{2-(1-methoxyethoxy)ethyl}amine, tris{2-(1-ethoxyethoxy)ethyl}amine, tris{2-(1-ethoxypropoxy)ethyl}amine, tris[2-{2-(2-hydroxyethoxy)ethoxy}ethyl]amine, 4,7,13,16,21,24-hexaoxa-1,10-diazabicyclo[8.8.8]hexacosane, 4,7,13,18-tetraoxa-1,10-diazabicyclo[8.5.5]eicosane, 1,4,10,13-tetraoxa-7,16-diazabicyclooctadecane, 1-aza-12-crown-4, 1-aza-15-crown-5, 1-aza-18-crown-6, tris(2-formyloxyethyl)amine, tris(2-acetoxyethyl)amine, tris(2-propionyloxyethyl)amine, tris(2-butyryloxyethyl)amine, tris(2-isobutyryloxyethyl)amine, tris(2-valeryloxyethyl)amine, tris(2-pivaloyloxyethyl)amine, N,N-bis(2-acetoxyethyl)-2-(acetoxyacetoxy)ethylamine, tris(2-methoxycarbonyloxyethyl)amine, tris(2-tert-butoxycarbonyloxyethyl)amine, tris[2-(2-oxopropoxy)ethyl]amine, tris[2-(methoxycarbonylmethyl)oxyethyl]amine, tris[2-(tert-butoxycarbonylmethyloxy)ethyl]amine, tris[2-(cyclohexyloxycarbonylmethyloxy)ethyl]amine, tris(2-methoxycarbonylethyl)amine, tris(2-ethoxycarbonylethyl)amine, N,N-bis(2-hydroxyethyl)-2-(methoxycarbonyl)ethylamine, N,N-bis(2-acetoxyethyl)-2-(methoxycarbonyl)ethylamine, N,N-bis(2-hydroxyethyl)-2-(ethoxycarbonyl)ethylamine, N,N-bis(2-acetoxyethyl)-2-(ethoxycarbonyl)ethylamine, N,N-bis(2-hydroxyethyl)-2-(2-methoxyethoxycarbonyl)ethylamine, N,N-bis(2-acetoxyethyl)-2-(2-methoxyethoxycarbonyl)ethylamine, N,N-bis(2-hydroxyethyl)-2-(2-hydroxyethoxycarbonyl)ethylamine, N,N-bis(2-acetoxyethyl)-2-(2-acetoxyethoxycarbonyl)ethylamine, N,N-bis(2-hydroxyethyl)-2-[(methoxycarbonyl)methoxycarbonyl]ethylamine, N,N-bis(2-acetoxyethyl)-2-[(methoxycarbonyl)methoxycarbonyl]-ethylamine, N,N-bis(2-hydroxyethyl)-2-(2-oxopropoxycarbonyl)ethylamine, N,N-bis(2-acetoxyethyl)-2-(2-oxopropoxycarbonyl)ethylamine, N,N-bis(2-hydroxyethyl)-2-(tetrahydrofurfuryloxycarbonyl)ethylamine, N,N-bis(2-acetoxyethyl)-2-(tetrahydrofurfuryloxycarbonyl)ethylamine, N,N-bis(2-hydroxyethyl)-2-[(2-oxotetrahydrofuran-3-yl)oxycarbonyl]ethylamine, N,N-bis(2-acetoxyethyl)-2-[(2-oxotetrahydrofuran-3-yl)oxycarbonyl]ethylamine, N,N-bis(2-hydroxyethyl)-2-(4-hydroxybutoxycarbonyl)ethylamine, N,N-bis(2-formyloxyethyl)-2-(4-formyloxybutoxycarbonyl)ethylamine, N,N-bis(2-formyloxyethyl)-2-(2-formyloxyethoxycarbonyl)ethylamine, N,N-bis(2-methoxyethyl)-2-(methoxycarbonyl)ethylamine, N-(2-hydroxyethyl)-bis[2-(methoxycarbonyl)

ethyl]amine, N-(2-acetoxyethyl)-bis[2-(methoxycarbonyl) ethyl]amine, N-(2-hydroxyethyl)-bis[2-(ethoxycarbonyl) ethyl]amine, N-(2-acetoxyethyl)-bis[2-(ethoxycarbonyl) ethyl]amine, N-(3-hydroxy-1-propyl)-bis[2-(methoxycarbonyl)ethyl]amine, N-(3-acetoxy-1-propyl)-bis [2-(methoxycarbonyl)ethyl]amine, N-(2-methoxyethyl)-bis [2-(methoxycarbonyl)ethyl]amine, N-butyl-bis[2-(methoxycarbonyl)ethyl]amine, N-butyl-bis[2-(2-methoxyethoxycarbonyl)ethyl]amine, N-methyl-bis(2-acetoxyethyl)amine, N-ethyl-bis(2-acetoxyethyl)amine, N-methyl-bis(2-pivaloyloxyethyl)amine, N-ethyl-bis[2-(methoxycarbonyloxy)ethyl]amine, N-ethyl-bis[2-(tert-butoxycarbonyloxy)ethyl]amine, tris(methoxycarbonylmethyl)amine, tris(ethoxycarbonylmethyl)amine, N-butyl-bis(methoxycarbonylmethyl)amine, N-hexyl-bis(methoxycarbonylmethyl)amine, and β-(diethylamino)-δ-valerolactone.

Also useful are one or more of cyclic structure-bearing basic compounds having the following general formula (B)-2.

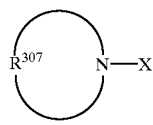
(B)-2

Herein X is as defined above, and $R^{307}$ is a straight or branched alkylene group of 2 to 20 carbon atoms which may contain one or more carbonyl, ether, ester or sulfide groups.

Illustrative examples of the cyclic structure-bearing basic compounds having formula (B)-2 include 1-[2-(methoxymethoxy)ethyl]pyrrolidine, 1-[2-(methoxymethoxy)ethyl]piperidine, 4-[2-(methoxymethoxy)ethyl]morpholine, 1-[2-[(2-methoxyethoxy)methoxy]ethyl]pyrrolidine, 1-[2-[(2-methoxyethoxy)methoxy]ethyl]piperidine, 4-[2-[(2-methoxyethoxy)methoxy]ethyl]morpholine, 2-(1-pyrrolidinyl)ethyl acetate, 2-piperidinoethyl acetate, 2-morpholinoethyl acetate, 2-(1-pyrrolidinyl)ethyl formate, 2-piperidinoethyl propionate, 2-morpholinoethyl acetoxyacetate, 2-(1-pyrrolidinyl)ethyl methoxyacetate, 4-[2-(methoxycarbonyloxy)ethyl]morpholine, 1-[2-(t-butoxycarbonyloxy)ethyl]piperidine, 4-[2-(2-methoxyethoxycarbonyloxy)ethyl]morpholine, methyl 3-(1-pyrrolidinyl)propionate, methyl 3-piperidinopropionate, methyl 3-morpholinopropionate, methyl 3-(thiomorpholino) propionate, methyl 2-methyl-3-(1-pyrrolidinyl)propionate, ethyl 3-morpholinopropionate, methoxycarbonylmethyl 3-piperidinopropionate, 2-hydroxyethyl 3-(1-pyrrolidinyl) propionate, 2-acetoxyethyl 3-morpholinopropionate, 2-oxotetrahydrofuran-3-yl 3-(1-pyrrolidinyl)propionate, tetrahydrofurfuryl 3-morpholinopropionate, glycidyl 3-piperidinopropionate, 2-methoxyethyl 3-morpholinopropionate, 2-(2-methoxyethoxy)ethyl 3-(1-pyrrolidinyl)propionate, butyl 3-morpholinopropionate, cyclohexyl 3-piperidinopropionate, α-(1-pyrrolidinyl) methyl-γ-butyrolactone, β-piperidino-γ-butyrolactone, β-morpholino-δ-valerolactone, methyl 1-pyrrolidinylacetate, methyl piperidinoacetate, methyl morpholinoacetate, methyl thiomorpholinoacetate, ethyl 1-pyrrolidinylacetate, and 2-methoxyethyl morpholinoacetate.

Also, one or more of cyano-bearing basic compounds having the following general formulae (B)-3 to (B)-6 may be blended.

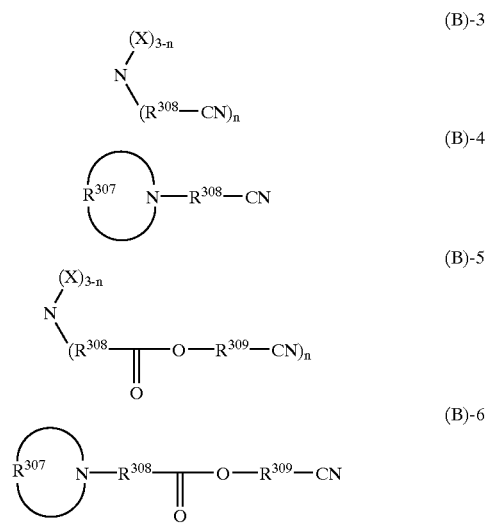

Herein, X, $R^{307}$ and n are as defined above, and $R^{308}$ and $R^{309}$ each are independently a straight or branched alkylene group of 1 to 4 carbon atoms.

Illustrative examples of the cyano-bearing basic compounds include 3-(diethylamino)propiononitrile, N,N-bis(2-hydroxyethyl)-3-aminopropiononitrile, N,N-bis(2-acetoxyethyl)-3-aminopropiononitrile, N,N-bis(2-formyloxyethyl)-3-aminopropiononitrile, N,N-bis(2-methoxyethyl)-3-aminopropiononitrile, N,N-bis[2-(methoxymethoxy)ethyl]-3-aminopropiononitrile, methyl N-(2-cyanoethyl)-N-(2-methoxyethyl)-3-aminopropanoate, methyl N-(2-cyanoethyl)-N-(2-hydroxyethyl)-3-aminopropionate, methyl N-(2-acetoxyethyl)-N-(2-cyanoethyl)-3-aminopropionate, N-(2-cyanoethyl)-N-ethyl-3-aminopropiononitrile, N-(2-cyanoethyl)-N-(2-hydroxyethyl)-3-aminopropiononitrile, N-(2-acetoxyethyl)-N-(2-cyanoethyl)-3-aminopropiononitrile, N-(2-cyanoethyl)-N-(2-formyloxyethyl)-3-aminopropiononitrile, N-(2-cyanoethyl)-N-(2-methoxyethyl)-3-aminopropiononitrile, N-(2-cyanoethyl)-N-[2-(methoxymethoxy)ethyl]-3-aminopropiononitrile, N-(2-cyanoethyl)-N-(3-hydroxy-1-propyl)-3-aminopropiononitrile, N-(3-acetoxy-1-propyl)-N-(2-cyanoethyl)-3-aminopropiononitrile, N-(2-cyanoethyl)-N-(3-formyloxy-1-propyl)-3-aminopropiononitrile, N-(2-cyanoethyl)-N-tetrahydrofurfuryl-3-aminopropiononitrile, N,N-bis(2-cyanoethyl)-3-aminopropiononitrile, diethylaminoacetonitrile, N,N-bis(2-hydroxyethyl) aminoacetonitrile, N,N-bis(2-acetoxyethyl) aminoacetonitrile, N,N-bis(2-formyloxyethyl) aminoacetonitrile, N,N-bis(2-methoxyethyl) aminoacetonitrile, N,N-bis[2-(methoxymethoxy)ethyl] aminoacetonitrile, methyl N-cyanomethyl-N-(2-methoxyethyl)-3-aminopropanoate, methyl N-cyanomethyl-N-(2-hydroxyethyl)-3-aminopropionate, methyl N-(2-acetoxyethyl)-N-cyanomethyl-3-aminopropionate, N-cyanomethyl-N-(2-hydroxyethyl)aminoacetonitrile, N-(2-acetoxyethyl)-N-(cyanomethyl)aminoacetonitrile, N-cyanomethyl-N-(2-formyloxyethyl)aminoacetonitrile, N-cyanomethyl-N-(2-methoxyethyl)aminoacetonitrile, N-cyanomethyl-N-[2-(methoxymethoxy)ethyl] aminoacetonitrile, N-cyanomethyl-N-(3-hydroxy-1-propyl) aminoacetonitrile, N-(3-acetoxy-1-propyl)-N-(cyanomethyl)aminoacetonitrile, N-cyanomethyl-N-(3-formyloxy-1-propyl)aminoacetonitrile, N,N-bis (cyanomethyl)aminoacetonitrile, 1-pyrrolidinepropiononitrile, 1-piperidinepropiononitrile, 4-morpholinepropiononitrile, 1-pyrrolidineacetonitrile, 1-piperidineacetonitrile, 4-morpholineacetonitrile, cyanomethyl 3-diethylaminopropionate, cyanomethyl N,N-bis(2-hydroxyethyl)-3-aminopropionate, cyanomethyl N,N-bis(2-acetoxyethyl)-3-aminopropionate, cyanomethyl N,N-bis(2-formyloxyethyl)-3-aminopropionate, cyanomethyl N,N-bis(2-methoxyethyl)-3-aminopropionate, cyanomethyl N,N-bis[2-(methoxymethoxy)ethyl]-3-aminopropionate, 2-cyanoethyl 3-diethylaminopropionate, 2-cyanoethyl N,N-bis(2-hydroxyethyl)-3-aminopropionate, 2-cyanoethyl N,N-bis(2-acetoxyethyl)-3-aminopropionate, 2-cyanoethyl N,N-bis(2-formyloxyethyl)-3-aminopropionate, 2-cyanoethyl N,N-bis(2-methoxyethyl)-3-aminopropionate, 2-cyanoethyl N,N-bis[2-(methoxymethoxy)ethyl]-3-aminopropionate, cyanomethyl 1-pyrrolidinepropionate, cyanomethyl 1-piperidinepropionate, cyanomethyl 4-morpholinepropionate, 2-cyanoethyl 1-pyrrolidinepropionate, 2-cyanoethyl 1-piperidinepropionate, and 2-cyanoethyl 4-morpholinepropionate.

These basic compounds may be used alone or in admixture of any. The basic compound is preferably formulated in an amount of 0.001 to 2 parts, and especially 0.01 to 1 part by weight, per 100 parts by weight of the base resin. Less than 0.001 part of the basic compound may fail to achieve the desired effects thereof, while the use of more than 2 parts would result in too low a sensitivity.

Component (E)

The dissolution inhibitor (E) is preferably selected from compounds possessing a weight average molecular weight of 100 to 1,000 and having on the molecule at least two phenolic hydroxyl groups, in which an average of from 10 to 100 mol % of all the hydrogen atoms on the phenolic hydroxyl groups are replaced with acid labile groups.

Illustrative, non-limiting, examples of the dissolution inhibitor (E) which are useful herein include bis(4-(2'-tetrahydropyranyloxy)phenyl)methane, bis(4-(2'-tetrahydrofuranyloxy)phenyl)methane, bis(4-tert-butoxyphenyl)methane, bis(4-tert-butoxycarbonyloxyphenyl)methane, bis(4-tert-butoxycarbonylmethyloxyphenyl)methane, bis(4-(1'-ethoxyethoxy)phenyl)methane, bis(4-(1'-ethoxypropyloxy)phenyl)methane, 2,2-bis(4'-(2"-tetrahydropyranyloxy))propane, 2,2-bis(4'-(2"-tetrahydrofuranyloxy)phenyl)propane, 2,2-bis(4'-tert-butoxyphenyl)propane, 2,2-bis(4'-tert-butoxycarbonyloxyphenyl)propane, 2,2-bis(4'-tert-butoxycarbonylmethyloxyphenyl)propane, 2,2-bis(4'-(1"-ethoxyethoxy)phenyl)propane, 2,2-bis(4'-(1"-ethoxypropyloxy)phenyl)propane, tert-butyl 4,4-bis(4'-(2"-tetrahydropyranyloxy)phenyl)valerate, tert-butyl 4,4-bis(4'-(2"-tetrahydrofuranyloxy)phenyl)valerate, tert-butyl 4,4-bis(4'-tert-butoxyphenyl)valerate, tert-butyl 4,4-bis(4'-tert-butoxycarbonyloxyphenyl)valerate, tert-butyl 4,4-bis(4'-tert-butoxycarbonylmethyloxyphenyl)valerate, tert-butyl 4,4-bis(4'-(1"-ethoxyethoxy)phenyl)valerate, tert-butyl 4,4-bis(4'-(1"-ethoxypropyloxy)phenyl)valerate, tris(4-(2'-tetrahydropyranyloxy)phenyl)methane, tris(4-(2'-tetrahydrofuranyloxy)phenyl)methane, tris(4-tert-butoxyphenyl)methane, tris(4-tert-butoxycarbonyloxyphenyl)methane, tris(4-tert-butoxycarbonyloxymethylphenyl)methane, tris(4-(1'-ethoxyethoxy)phenyl)methane, tris(4-(1'-ethoxypropyloxy)phenyl)methane, 1,1,2-tris(4'-(2"-tetrahydropyranyloxy)phenyl)ethane, 1,1,2-tris(4'-(2"-tetrahydrofuranyloxy)phenyl)ethane, 1,1,2-tris(4'-tert-butoxyphenyl)ethane, 1,1,2-tris(4'-tert-butoxycarbonyloxyphenyl)ethane, 1,1,2-tris(4'-tert-butoxycarbonylmethyloxyphenyl)ethane, 1,1,2-tris(4'-(1'-ethoxyethoxy)phenyl)ethane, and 1,1,2-tris(4'-(1'-ethoxypropyloxy)phenyl)ethane.

The compounds serving as dissolution inhibitor have a weight average molecular weight of 100 to 1,000, preferably 150 to 800. An appropriate amount of the dissolution inhibitor (E) is 0 to about 50 parts, preferably about 5 to 50 parts, and especially about 10 to 30 parts by weight per 100 parts by weight of the base resin. Less amounts of the dissolution inhibitor may fail to yield an improved resolution, whereas too much amounts would lead to slimming of the patterned film, and thus a decline in resolution. The inhibitor may be used singly or as a mixture of two or more thereof.

The resist composition of the invention may include optional ingredients, typically a surfactant which is commonly used for improving the coating characteristics. Optional ingredients may be added in conventional amounts so long as this does not compromise the objects of the invention.

Illustrative, non-limiting, examples of the surfactant include nonionic surfactants, for example, polyoxyethylene alkyl ethers such as polyoxyethylene lauryl ether, polyoxyethylene stearyl ether, polyoxyethylene cetyl ether, and polyoxyethylene oleyl ether, polyoxyethylene alkylaryl ethers such as polyoxyethylene octylphenol ether and polyoxyethylene nonylphenol ether, polyoxyethylene polyoxypropylene block copolymers, sorbitan fatty acid esters such as sorbitan monolaurate, sorbitan monopalmitate, and sorbitan monostearate, and polyoxyethylene sorbitan fatty acid esters such as polyoxyethylene sorbitan monolaurate, polyoxyethylene sorbitan monopalmitate, polyoxyethylene sorbitan monostearate, polyoxyethylene sorbitan trioleate, and polyoxyethylene sorbitan tristearate; fluorochemical surfactants such as EFTOP EF301, EF303 and EF352 (Tohkem Products Co., Ltd.), Megaface F171, F172 and F173 (Dai-Nippon Ink & Chemicals, Inc.), Florade FC430 and FC431 (Sumitomo 3M Co., Ltd.), Asahiguard AG710, Surflon S-381, S-382, SC101, SC102, SC103, SC104, SC105, SC106, Surfynol E1004, KH-10, KH-20, KH-30 and KH-40 (Asahi Glass Co., Ltd.); organosiloxane polymers KP341, X-70-092 and X-70-093 (Shin-Etsu Chemical Co., Ltd.), acrylic acid or methacrylic acid Polyflow No. 75 and No. 95 (Kyoeisha Ushi Kagaku Kogyo Co., Ltd.). Inter alia, FC430, Surflon S-381, Surfynol E1004, KH-20 and KH-30 are preferred. These surfactants may be used alone or in admixture.

Pattern formation using the resist composition of the invention may be carried out by a known lithographic technique. For example, the resist composition may be applied onto a substrate such as a silicon wafer by spin coating or the like to form a resist film having a thickness of 0.1 to 1.0 µm, which is then pre-baked on a hot plate at 60 to 200° C. for 10 seconds to 10 minutes, and preferably at 80 to 150° C. for ½ to 5 minutes. A patterning mask having the desired pattern may then be placed over the resist film, and the film exposed through the mask to an electron beam or to high-energy radiation such as deep-UV rays, excimer laser beams, or x-rays in a dose of about 1 to 200 mJ/cm$^2$, and preferably about 10 to 100 mJ/cm$^2$, then post-exposure baked (PEB) on a hot plate at 60 to 150° C. for 10 seconds to 5 minutes, and preferably at 80 to 130° C. for ½ to 3 minutes. Finally, development may be carried out using as the developer an aqueous alkali solution, such as 0.1 to 5%, and preferably 2 to 3%, tetramethylammonium hydroxide (TMAH), this being done by a conventional method such as dipping, puddling, or spraying for a period of 10 seconds to 3 minutes, and preferably 30 seconds to 2 minutes. These steps result in the formation of the desired pattern on the substrate.

Of the various types of high-energy radiation that may be used, the resist composition of the invention is best suited to micro-pattern formation with, in particular, deep-UV rays having a wavelength of 254 to 120 nm, an excimer laser, especially ArF excimer laser (193 nm), $F_2$ excimer laser (157 nm), $Kr_2$ excimer laser (146 nm), KrAr excimer laser (134 nm) or $Ar_2$ excimer laser (126 nm), x-rays, or an electron beam. Recommended is exposure to high-energy radiation in a wavelength band of 100 to 180 nm or 1 to 30 nm, specifically $F_2$ laser beam, $Ar_2$ laser beam or soft x-ray. The desired pattern may not be obtainable outside the upper and lower limits of the above range.

The resist composition of the invention is sensitive to high-energy radiation and exhibits a high sensitivity at a wavelength of up to 200 nm, especially up to 170 nm. Due to the use of a polymer of a sulfonic acid ester or a sulfone-containing compound as a base resin, the resist composition is improved in transparency, adhesion and developer penetration as well as plasma etching resistance. These features, combined with the reduced absorption at the exposure wavelength of a $F_2$ laser, permit the inventive resist composition to easily form a finely defined pattern having sidewalls perpendicular to the substrate, making the resist ideal as a micropatterning material in VLSI fabrication.

EXAMPLE

Examples of the invention are given below by way of illustration and not by way of limitation. The abbreviations used herein are AIBN for 2,2'-azobisisobutyronitrile, GPC for gel permeation chromatography, NMR for nuclear magnetic resonance, Mw for weight average molecular weight, and Mn for number average molecular weight. Mw/Mn is a molecular weight distribution or dispersity.

Monomer Synthesis Example 1
Synthesis of Monomer 1

In a 1-liter four necked flask, 31.0 g of an alcohol shown below and 17.4 g of pyridine were dissolved in 100 g of dichloromethane together with a polymerization stabilizer. While the flask was immersed in an ice bath to keep the internal temperature below 10° C., 2-chloroethanesulfonyl chloride was added dropwise to the flask. Conventional post treatment was carried out. The resulting oily matter was purified by silica gel chromatography, obtaining 24.8 g of Monomer 1. The yield was 61%.

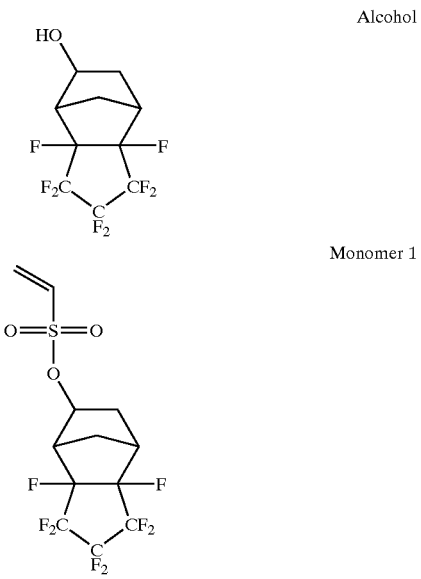

Analytical data of Monomer 1
$^1$H-NMR (CDCl$_3$, 270 MHz): δ 1.24–3.17 (m, 6H), 4.72 (d, 0.4H), 5.00 (d, 0.6H), 6.19 (d, 1H), 6.40–6.60 (m, 2H)
FT-IR (NaCl): 3116, 3070, 2979, 2942, 1614, 1484, 1475, 1450, 1371, 1353, 1334, 1319, 1295, 1280, 1265, 1213, 1174, 1139, 1110, 1064, 1035, 1004, 981, 964, 952, 917, 875, 846, 813, 736, 671 cm$^{-1}$

Polymer Synthesis Example 1
Copolymerization of Monomer 1 and Monomer 2 (30:70) and Protection Reaction on Hydroxyl Groups in the Polymer A 300-ml flask was charged with 7.53 g of Monomer 1 and 12.47 g of Monomer 2, shown below, which were dissolved in 8.6 g of toluene. The system was fully purged of oxygen, charged with 0.21 g of the initiator AIBN, and heated at 60° C. at which polymerization reaction took place for 24 hours.

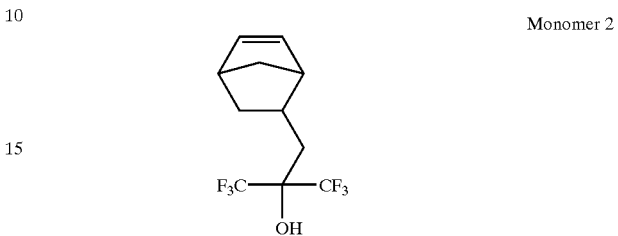

The polymer thus obtained was worked up by pouring the reaction mixture into hexane whereupon the polymer precipitated. The procedure of dissolving the polymer in tetrahydrofuran (THF) and pouring in 3 liters of hexane for precipitation was repeated twice, after which the polymer was separated and dried. There was obtained 14.8 g of a white polymer, which was found to have a Mw of 5,500 as measured by the light scattering method, and a dispersity (Mw/Mn) of 1.5 as determined from the GPC elution curve. On $^1$H-NMR analysis, the polymer was found to consist of Monomer 1 and Monomer 2 in a molar ratio of 29:71.

Next, a 300-ml flask was charged with 10.0 g of the thus obtained polymer and 0.61 g of pyridine, which were dissolved in 40 g of THF. To the flask at room temperature, 1.70 g of di-tert-butyl dicarbonate in 5 g of THF was added dropwise. The contents were stirred for one hour at room temperature.

The polymer thus obtained was worked up by pouring the reaction mixture into methanol whereupon the polymer precipitated. The procedure of dissolving the polymer in THF and pouring in 3 liters of methanol for precipitation was repeated twice, after which the polymer was separated and dried. There was obtained 8.3 g of a white polymer, which was found to have a Mw of 5,700 as measured by the light scattering method, and a dispersity (Mw/Mn) of 1.5 as determined from the GPC elution curve. On $^1$H-NMR analysis of the polymer, it was found that 29% of hydroxyl groups had been substituted with tert-butoxycarbonyl groups (abbreviated as Boc groups, hereinafter).

Polymer Synthesis Example 2
Copolymerization of Monomer 1, Monomer 2 and Tert-Butyl α-Trifluoromethylacrylate (20:40:40)

A 300-ml flask was charged with 5.82 g of Monomer 1, 8.27 g of Monomer 2, and 5.91 g of tert-butyl α-trifluoromethylacrylate, which were dissolved in 8.6 g of toluene. The system was fully purged of oxygen, charged with 0.25 g of the initiator AIBN, and heated at 60° C. at which polymerization reaction took place for 24 hours.

The polymer thus obtained was worked up by pouring the reaction mixture into hexane whereupon the polymer precipitated. The procedure of dissolving the polymer in THF and pouring in 3 liters of hexane for precipitation was repeated twice, after which the polymer was separated and dried. There was obtained 15.1 g of a white polymer, which was found to have a Mw of 5,900 as measured by the light scattering method, and a dispersity (Mw/Mn) of 1.5 as determined from the GPC elution curve. On $^1$H-NMR analysis, the polymer was found to consist of Monomer 1, Monomer 2 and tert-butyl α-trifluoromethylacrylate in a molar ratio of 19:41:40.

Polymer Synthesis Example 3
Copolymerization of Monomer 1, Monomer 2 and 2-Methyladamantyl α-Trifluoromethylacrylate (20:40:40)

A 300-ml flask was charged with 5.11 g of Monomer 1, 7.26 g of Monomer 2, and 7.63 g of 2-methyladamantyl α-trifluoromethylacrylate, which were dissolved in 8.6 g of toluene. The system was fully purged of oxygen, charged with 0.22 g of the initiator AIBN, and heated at 60° C. at which polymerization reaction took place for 24 hours.

The polymer thus obtained was worked up by pouring the reaction mixture into hexane whereupon the polymer precipitated. The procedure of dissolving the polymer in THF and pouring in 3 liters of hexane for precipitation was repeated twice, after which the polymer was separated and dried. There was obtained 15.3 g of a white polymer, which was found to have a Mw of 5,700 as measured by the light scattering method, and a dispersity (Mw/Mn) of 1.5 as determined from the GPC elution curve. On $^1$H-NMR analysis, the polymer was found to consist of Monomer 1, Monomer 2 and 2-methyladamantyl α-trifluoromethylacrylate in a molar ratio of 18:41:41.

Polymer Synthesis Example 4
Copolymerization of Monomer 1 and Monomer 3 (30:70) and Protection Reaction on Hydroxyl Groups in the Polymer A 300-ml flask was charged with 7.60 g of Monomer 1 and 12.40 g of Monomer 3, which were dissolved in 8.6 g of toluene. The system was fully purged of oxygen, charged with 0.22 g of the initiator AIBN, and heated at 60° C. at which polymerization reaction took place for 24 hours.

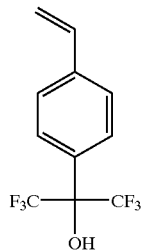

Monomer 3

The polymer thus obtained was worked up by pouring the reaction mixture into hexane whereupon the polymer precipitated. The procedure of dissolving the polymer in THF and pouring in 3 liters of hexane for precipitation was repeated twice, after which the polymer was separated and dried. There was obtained 15.3 g of a white polymer, which was found to have a Mw of 5,500 as measured by the light scattering method, and a dispersity (Mw/Mn) of 1.5 as determined from the GPC elution curve. On $^1$H-NMR analysis, the polymer was found to consist of Monomer 1 and Monomer 3 in a molar ratio of 29:71.

Next, a 300-ml flask was charged with 10.0 g of the thus obtained polymer and 0.62 g of pyridine, which were dissolved in 40 g of THF. To the flask at room temperature, 1.72 g of di-tert-butyl dicarbonate in 5 g of THF was added dropwise. The contents were stirred for one hour at room temperature.

The polymer thus obtained was worked up by pouring the reaction mixture into methanol whereupon the polymer precipitated. The procedure of dissolving the polymer in THF and pouring in 3 liters of methanol for precipitation was repeated twice, after which the polymer was separated and dried. There was obtained 8.3 g of a white polymer, which was found to have a Mw of 5,700 as measured by the light scattering method, and a dispersity (Mw/Mn) of 1.5 as determined from the GPC elution curve. On $^1$H-NMR analysis of the polymer, it was found that 29% of hydroxyl groups had been substituted with Boc groups.

Polymer Synthesis Example 5
Copolymerization of Monomer 1, Monomer 3 and Tert-Butyl α-Trifluoromethylacrylate (10:50:40)

A 300-ml flask was charged with 3.06 g of Monomer 1, 10.72 g of Monomer 3, and 6.22 g of tert-butyl α-trifluoromethylacrylate, which were dissolved in 8.6 g of toluene. The system was fully purged of oxygen, charged with 0.26 g of the initiator AIBN, and heated at 60° C. at which polymerization reaction took place for 24 hours.

The polymer thus obtained was worked up by pouring the reaction mixture into hexane whereupon the polymer precipitated. The procedure of dissolving the polymer in THF and pouring in 3 liters of hexane for precipitation was repeated twice, after which the polymer was separated and dried. There was obtained 14.3 g of a white polymer, which was found to have a Mw of 5,200 as measured by the light scattering method, and a dispersity (Mw/Mn) of 1.5 as determined from the GPC elution curve. On $^1$H-NMR analysis, the polymer was found to consist of Monomer 1, Monomer 3 and tert-butyl α-trifluoromethylacrylate in a molar ratio of 19:51:40.

Polymer Synthesis Example 6
Copolymerization of Monomer 1, Monomer 3 and 2-Methyladamantyl α-Trifluoromethylacrylate (10:50:40)

A 300-ml flask was charged with 2.67 g of Monomer 1, 9.35 g of Monomer 3, and 7.98 g of 2-methyladamantyl α-trifluoromethylacrylate, which were dissolved in 8.6 g of toluene. The system was fully purged of oxygen, charged with 0.23 g of the initiator AIBN, and heated at 60° C. at which polymerization reaction took place for 24 hours.

The polymer thus obtained was worked up by pouring the reaction mixture into hexane whereupon the polymer precipitated. The procedure of dissolving the polymer in THF and pouring in 3 liters of hexane for precipitation was repeated twice, after which the polymer was separated and dried. There was obtained 14.5 g of a white polymer, which was found to have a Mw of 5,700 as measured by the light scattering method, and a dispersity (Mw/Mn) of 1.5 as determined from the GPC elution curve. On $^1$H-NMR analysis, the polymer was found to consist of Monomer 1, Monomer 3 and 2-methyladamantyl α-trifluoromethylacrylate in a molar ratio of 20:51:39.

Polymer Synthesis Example 7
Copolymerization of Monomer 4, Monomer 2 and Tert-Butyl α-Trifluoromethylacrylate (30:30:40)

A 300-ml flask was charged with 6.23 g of Monomer 4, shown below, 7.05 g of Monomer 2, and 6.73 g of tert-butyl α-trifluoromethylacrylate, which were dissolved in 8.6 g of toluene. The system was fully purged of oxygen, charged with 0.28 g of the initiator AIBN, and heated at 60° C. at which polymerization reaction took place for 24 hours.

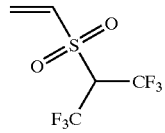

Monomer 4

The polymer thus obtained was worked up by pouring the reaction mixture into hexane whereupon the polymer precipitated. The procedure of dissolving the polymer in THF and pouring in 3 liters of hexane for precipitation was repeated twice, after which the polymer was separated and dried. There was obtained 14.4 g of a white polymer, which was found to have a Mw of 6,200 as measured by the light scattering method, and a dispersity (Mw/Mn) of 1.5 as determined from the GPC elution curve. On $^1$H-NMR analysis, the polymer was found to consist of Monomer 4, Monomer 2 and tert-butyl α-trifluoromethylacrylate in a molar ratio of 28:31:41.

Polymer Synthesis Example 8
Copolymerization of Monomer 5, Monomer 2 and Tert-Butyl α-Trifluoromethylacrylate (30:30:40)

A 300-ml flask was charged with 8.17 g of Monomer 5, shown below, 6.05 g of Monomer 2, and 5.77 g of tert-butyl α-trifluoromethylacrylate, which were dissolved in 8.6 g of toluene. The system was fully purged of oxygen, charged with 0.24 g of the initiator AIBN, and heated at 60° C. at which polymerization reaction took place for 24 hours.

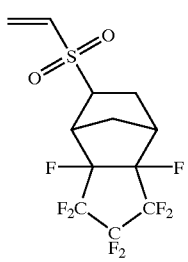

Monomer 5

The polymer thus obtained was worked up by pouring the reaction mixture into hexane whereupon the polymer precipitated. The procedure of dissolving the polymer in THF and pouring in 3 liters of hexane for precipitation was repeated twice, after which the polymer was separated and dried. There was obtained 14.9 g of a white polymer, which was found to have a Mw of 6,700 as measured by the light scattering method, and a dispersity (Mw/Mn) of 1.5 as determined from the GPC elution curve. On $^1$H-NMR analysis, the polymer was found to consist of Monomer 5, Monomer 2 and tert-butyl α-trifluoromethylacrylate in a molar ratio of 29:30:41.

Polymer Synthesis Example 9
Copolymerization of Monomer 3, Monomer 4 and Tert-Butyl α-Trifluoromethylacrylate (50:10:40)

A 300-ml flask was charged with 11.36 g of Monomer 3, 2.04 g of Monomer 4, and 6.6 g of tert-butyl α-trifluoromethylacrylate, which were dissolved in 30 g of toluene. The system was fully purged of oxygen, charged with 0.28 g of the initiator AIBN, and heated at 60° C. at which polymerization reaction took place for 24 hours.

The polymer thus obtained was worked up by pouring the reaction mixture into hexane whereupon the polymer precipitated. The procedure of dissolving the polymer in THF and pouring in 3 liters of hexane for precipitation was repeated twice, after which the polymer was separated and dried. There was obtained 15.9 g of a white polymer, which was found to have a Mw of 7,700 as measured by the light scattering method, and a dispersity (Mw/Mn) of 1.5 as determined from the GPC elution curve. On $^1$H-NMR analysis, the polymer was found to consist of Monomer 3, Monomer 4 and tert-butyl α-trifluoromethylacrylate in a molar ratio of 51:11:38.

Polymer Synthesis Example 10
Copolymerization of Monomer 3, Monomer 5 and Tert-Butyl α-Trifluoromethylacrylate (50:10:40)

A 300-ml flask was charged with 10.78 g of Monomer 3, 2.96 g of Monomer 5, and 6.3 g of tert-butyl α-trifluoromethylacrylate, which were dissolved in 30 g of toluene. The system was fully purged of oxygen, charged with 0.26 g of the initiator AIBN, and heated at 60° C. at which polymerization reaction took place for 24 hours.

The polymer thus obtained was worked up by pouring the reaction mixture into hexane whereupon the polymer precipitated. The procedure of dissolving the polymer in THF and pouring in 3 liters of hexane for precipitation was repeated twice, after which the polymer was separated and dried. There was obtained 15.2 g of a white polymer, which was found to have a Mw of 7,200 as measured by the light scattering method, and a dispersity (Mw/Mn) of 1.5 as determined from the GPC elution curve. On $^1$H-NMR analysis, the polymer was found to consist of Monomer 3, Monomer 5 and tert-butyl α-trifluoromethylacrylate in a molar ratio of 51:10:39.

Polymer Synthesis Example 11
Copolymerization of Monomer 6, Monomer 7 and Tert-Butyl α-Trifluoromethylacrylate (30:30:40)

A 300-ml flask was charged with 7.27 g of Monomer 6, 6.56 g of Monomer 7, both shown below, and 6.17 g of tert-butyl α-trifluoromethylacrylate, which were dissolved in 8.6 g of 1,4-dioxane. The system was fully purged of oxygen, charged with 0.39 g of the initiator 2,2'-azobis(2,4-dimethylvaleronitrile), and heated at 60° C. at which polymerization reaction took place for 24 hours.

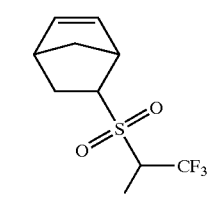

Monomer 6

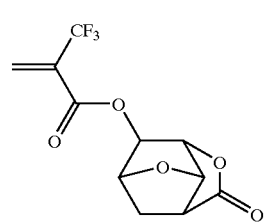

Monomer 7

The polymer thus obtained was worked up by pouring the reaction mixture into hexane whereupon the polymer precipitated. The procedure of dissolving the polymer in THF and pouring in 3 liters of hexane for precipitation was repeated twice, after which the polymer was separated and dried. There was obtained 14.4 g of a white polymer, which was found to have a Mw of 6,600 as measured by the light scattering method, and a dispersity (Mw/Mn) of 1.5 as determined from the GPC elution curve. On $^1$H-NMR analysis, the polymer was found to consist of Monomer 6, Monomer 7 and tert-butyl α-trifluoromethylacrylate in a molar ratio of 29:30:41.

Polymer Synthesis Example 12
Copolymerization of Monomer 8, Monomer 7 and Tert-Butyl α-Trifluoromethylacrylate (30:30:40)

A 300-ml flask was charged with 8.94 g of Monomer 8, shown below, 7.70 g of Monomer 7, and 5.36 g of tert-butyl α-trifluoromethylacrylate, which were dissolved in 8.6 g of 1,4-dioxane. The system was fully purged of oxygen, charged with 0.34 g of the initiator 2,2'-azobis(2,4-dimethylvaleronitrile), and heated at 60° C. at which polymerization reaction took place for 24 hours.

Monomer 8

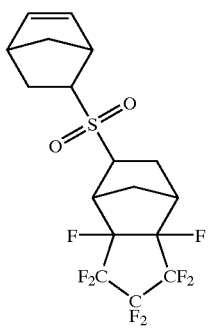

The polymer thus obtained was worked up by pouring the reaction mixture into hexane whereupon the polymer precipitated. The procedure of dissolving the polymer in THF and pouring in 3 liters of hexane for precipitation was repeated twice, after which the polymer was separated and dried. There was obtained 16.1 g of a white polymer, which was found to have a Mw of 6,900 as measured by the light scattering method, and a dispersity (Mw/Mn) of 1.5 as determined from the GPC elution curve. On $^1$H-NMR analysis, the polymer was found to consist of Monomer 8, Monomer 7 and tert-butyl α-trifluoromethylacrylate in a molar ratio of 29:30:41.

Evaluation

Polymer Transmittance Measurement

The polymers obtained in Polymer Synthesis Examples 1 to 12, designated Polymers 1 to 12, respectively, were determined for transmittance. Three other polymers were furnished for comparison purposes. Comparative Polymer 1 is a monodisperse polyhydroxystyrene having a molecular weight of 10,000 and a dispersity (Mw/Mn) of 1.1 in which 30% of hydroxyl groups are replaced by tetrahydropyranyl groups. Similarly, Comparative Polymer 2 is polymethyl methacrylate having a molecular weight of 15,000 and a dispersity (Mw/Mn) of 1.7; and Comparative Polymer 3 is a novolac polymer having a meta/para ratio of 40/60, a molecular weight of 9,000 and a dispersity (Mw/Mn) of 2.5.

Each polymer, 1 g, was thoroughly dissolved in 20 g of propylene glycol monomethyl ether acetate (PGMEA), and passed through a 0.2-μm filter, obtaining a polymer solution. The polymer solution was spin coated onto a MgF$_2$ substrate and baked on a hot plate at 100° C. for 90 seconds, forming a polymer film of 100 nm thick on the substrate. Using a vacuum ultraviolet spectrometer (VUV-200S by Nihon Bunko Co., Ltd.), the polymer film was measured for transmittance at 248 nm, 193 nm and 157 nm. The results are shown in Table 1.

TABLE 1

| | Transmittance (%) | | |
|---|---|---|---|
| | 248 nm | 193 nm | 157 nm |
| Polymer 1 | 99 | 91 | 60 |
| Polymer 2 | 99 | 90 | 55 |
| Polymer 3 | 99 | 91 | 49 |
| Polymer 4 | 99 | 8 | 50 |
| Polymer 5 | 99 | 15 | 50 |
| Polymer 6 | 99 | 14 | 48 |
| Polymer 7 | 99 | 90 | 55 |
| Polymer 8 | 99 | 91 | 61 |
| Polymer 9 | 99 | 90 | 52 |
| Polymer 10 | 99 | 91 | 54 |
| Polymer 11 | 99 | 89 | 54 |
| Polymer 12 | 99 | 90 | 56 |
| Comparative Polymer 1 | 90 | 5 | 15 |

TABLE 1-continued

| | Transmittance (%) | | |
|---|---|---|---|
| | 248 nm | 193 nm | 157 nm |
| Comparative Polymer 2 | 91 | 80 | 12 |
| Comparative Polymer 3 | 82 | 6 | 17 |

It is evident from Table 1 that resist materials using the inventive polymers maintain sufficient transparency at the F$_2$ excimer laser wavelength (157 nm).

Resist Preparation and Exposure

Resist solutions were prepared in a conventional manner by dissolving amounts as shown in Table 2 of the polymer, photoacid generator (PAG1 or PAG2), basic compound, and dissolution inhibitor (DRI1) in 1,000 parts of propylene glycol monomethyl ether acetate (PGMEA).

PAG1

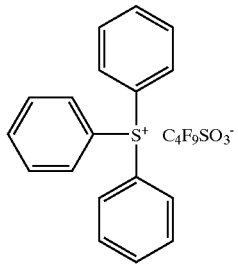

PAG2

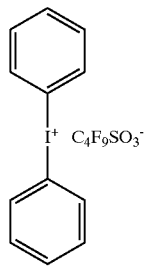

DRI1

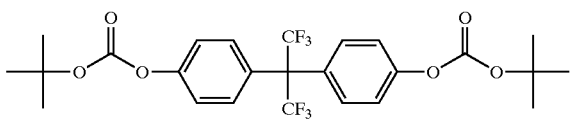

On silicon wafers having a film of DUV-30 (Brewer Science) coated to a thickness of 85 nm, the resist solutions were spin coated, then baked on a hot plate at 120° C. for 90 seconds to give resist films having a thickness of 100 nm.

The resist films were exposed by means of an F$_2$ excimer laser (VUVES-4500 by Lithotec Japan Co., Ltd.) while varying the exposure dose. Immediately after exposure, the resist films were baked (PEB) at 120° C. for 90 seconds and then developed for 60 seconds with a 2.38% aqueous solution of tetramethylammonium hydroxide. The film thickness was measured in different dose areas. From the residual film thickness-to-dose relationship, the sensitivity (Eth) was determined as the exposure dose giving a film thickness 0. A γ value which was the slope (tan θ) of the characteristic curve was also determined.

Separately, through a mask having a Cr pattern formed on a MgF$_2$ substrate, the resist film in close contact with the Cr pattern surface was exposed to a F$_2$ laser for effecting contact exposure. The exposure was followed by similar PEB and development, forming a pattern. A cross section of the pattern was observed under SEM, the ascertainable minimum pattern size giving a resolution.

TABLE 2

| polymer (pbw) | Photoacid generator (pbw) | Basic compound (pbw) | Dissolution inhibitor (pbw) | Solvent (pbw) | Eth, mJ/cm$^2$ | γ |
|---|---|---|---|---|---|---|
| Polymer 1 (100) | PAG1 (4) | tributylamine (0.1) | — | PGMEA (1000) | 10 | 6.5 |
| Polymer 2 (100) | PAG1 (4) | tributylamine (0.1) | — | PGMEA (1000) | 15 | 10.5 |
| Polymer 3 (100) | PAG1 (4) | tributylamine (0.1) | — | PGMEA (1000) | 12 | 12.8 |
| Polymer 4 (100) | PAG1 (4) | tributylamine (0.1) | — | PGMEA (1000) | 4 | 8.5 |
| Polymer 5 (100) | PAG1 (4) | tributylamine (0.1) | — | PGMEA (1000) | 5.5 | 9.8 |
| Polymer 6 (100) | PAG1 (4) | tributylamine (0.1) | — | PGMEA (1000) | 4.2 | 10.2 |
| Polymer 7 (100) | PAG1 (4) | tributylamine (0.1) | — | PGMEA (1000) | 25 | 10 |
| Polymer 8 (100) | PAG1 (4) | tributylamine (0.1) | — | PGMEA (1000) | 35 | 16 |
| Polymer 9 (100) | PAG1 (4) | tributylamine (0.1) | — | PGMEA (1000) | 16 | 8 |
| Polymer 10 (100) | PAG1 (4) | tributylamine (0.1) | — | PGMEA (1000) | 22 | 16 |
| Polymer 11 (100) | PAG1 (4) | tributylamine (0.1) | — | PGMEA (1000) | 31 | 18 |
| Polymer 12 (100) | PAG1 (4) | tributylamine (0.1) | — | PGMEA (1000) | 36 | 22 |
| Polymer 2 (100) | PAG1 (4) | triethanolamine (0.1) | — | PGMEA (1000) | 16 | 11.8 |
| Polymer 2 (100) | PAG1 (4) | tributylamine (0.1) | DRI1 (10) | PGMEA (1000) | 10 | 10.3 |
| Polymer 2 (100) | PAG2 (4) | tributylamine (0.1) | — | PGMEA (1000) | 22 | 12.5 |
| Polymer 7 (100) | PAG1 (4) | triethanolamine (0.1) | — | PGMEA (1000) | 29 | 15 |
| Polymer 7 (100) | PAG1 (4) | tributylamine (0.1) | DRI1 (10) | PGMEA (1000) | 20 | 8 |
| Polymer 7 (100) | PAG2 (4) | tributylamine (0.1) | — | PGMEA (1000) | 16 | 26 |
| Comparative Polymer 1 (100) | PAG1 (4) | triethanolamine (0.1) turned | — | PGMEA (1000) | non-sensitive, negative without film thickness decreasing to 0 nm | — |

Upon exposure to VUVES, the resist compositions within the scope of the invention exhibited high gamma values and high contrast and exerted the positive working effect that the film thickness decreased with an increasing exposure dose. The resolving power upon contact exposure was high.

Japanese Patent Application Nos. 2002-083943 and 2002-084093 are incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

What is claimed is:

1. A sulfonate compound having the following general formula (1):

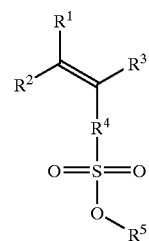
(1)

wherein $R^1$ to $R^3$ each are hydrogen, fluorine or a straight, branched or cyclic alkyl or fluorinated alkyl group of 1 to 20 carbon atoms, $R^4$ is a valence bond or a straight, branched or cyclic alkylene or fluorinated alkylene group of 1 to 20 carbon atoms, and $R^5$ is a branched or cyclic fluorinated alkyl group of 1 to 30 carbon atoms.

2. The sulfonate compound having the following general formula (1a):

(1a)

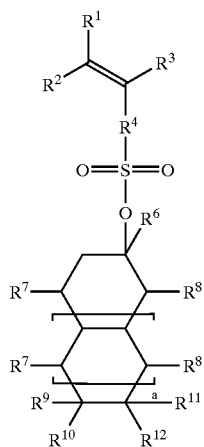

wherein $R^1$ to $R^3$ each are hydrogen, fluorine or a straight, branched or cyclic alkyl or fluorinated alkyl group of 1 to 20 carbon atoms, $R^4$ is a valence bond or a straight, branched or cyclic alkylene or fluorinated alkylene group of 1 to 20 carbon atoms, $R^6$ to $R^8$ each are hydrogen, fluorine or a straight, branched or cyclic alkyl or fluorinated alkyl group of 1 to 20 carbon atoms, or $R^7$ and $R^8$ may bond together to form a ring, and in that event, each is an alkylene group of 1 to 20 carbon atoms which may contain a hetero atom such as oxygen, sulfur or nitrogen, $R^9$ to $R^{12}$ each are hydrogen, fluorine or a straight, branched or cyclic alkyl or fluorinated alkyl group of 1 to 20 carbon atoms, at least one of $R^9$ to $R^{12}$ containing at least one fluorine atom, or two of $R^9$ to $R^{12}$ may bond together to form a ring, and in that event, each is a straight, branched or cyclic alkylene or fluorinated alkylene group of 1 to 20 carbon atoms, and "a" is 0 or 1.

3. The sulfonate compound having the following general formula (1b):

(1b)

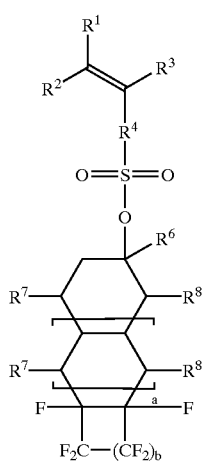

wherein $R^1$ to $R^3$ each are hydrogen, fluorine or a straight, branched or cyclic alkyl or fluorinated alkyl group of 1 to 20 carbon atoms, $R^4$ is a valence bond or a straight, branched or cyclic alkylene or fluorinated alkylene group of 1 to 20 carbon atoms, $R^6$ to $R^8$ each are hydrogen, fluorine or a straight, branched or cyclic alkyl or fluorinated alkyl group of 1 to 20 carbon atoms, or $R^7$ and $R^8$ may bond together to form a ring, and in that event, each is an alkylene group of 1 to 20 carbon atoms which may contain a hetero atom such as oxygen, sulfur or nitrogen, "a" is 0 or 1, and "b" is an integer of 2 to 4.

4. A polymer comprising recurring units of the following general formula (2) and having a weight average molecular weight of 1,000 to 500,000, (2)

wherein $R^1$ to $R^3$ each are hydrogen, fluorine or a straight, branched or cyclic alkyl or fluorinated alkyl group of 1 to 20 carbon atoms, $R^4$ is a valence bond or a straight, branched or cyclic alkylene or fluorinated alkylene group of 1 to 20 carbon atoms, $R^5$ is a branched or cyclic fluorinated alkyl group of 1 to 30 carbon atoms, and X is a valence bond or O.

5. The polymer of claim 4 comprising recurring units of the following general formula (2a):

(2a)

wherein $R^1$ to $R^3$ each are hydrogen, fluorine or a straight, branched or cyclic alkyl or fluorinated alkyl group of 1 to 20 carbon atoms, $R^4$ is a valence bond or a straight, branched or cyclic alkylene or fluorinated alkylene group of 1 to 20 carbon atoms, $R^6$ to $R^8$ each are hydrogen, fluorine or a straight, branched or cyclic alkyl or fluorinated alkyl group of 1 to 20 carbon atoms, or $R^7$ and $R^8$ may bond together to form a ring, and in that event, each is an alkylene group of 1 to 20 carbon atoms which may contain a hetero atom such as oxygen, sulfur or nitrogen, $R^9$ to $R^{12}$ each are hydrogen, fluorine or a straight, branched or cyclic alkyl or fluorinated alkyl group of 1 to 20 carbon atoms, at least one of $R^9$ to $R^{12}$ containing at least one fluorine atom, or two of $R^9$ to $R^{12}$ may bond together to form a ring, and in that event, each is a straight, branched or cyclic fluoronated alkylene group of 1 to 20 carbon atoms, "a" is 0 or 1, and X is a valence bond or O.

6. The polymer comprising recurring units of the following general formula (2b):

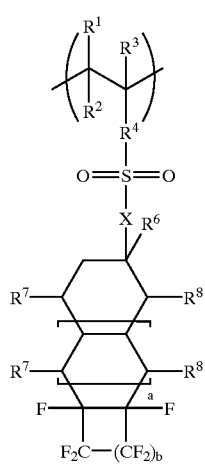

(2b)

wherein $R^1$ to $R^3$ each are hydrogen, fluorine or a straight, branched or cyclic alkyl or fluorinated alkyl group of 1 to 20 carbon atoms, $R^4$ is a valence bond or a straight, branched or cyclic alkylene or fluorinated alkylene group of 1 to 20 carbon atoms, $R^6$ to $R^8$ each are hydrogen, fluorine or a straight, branched or cyclic alkyl or fluorinated alkyl group of 1 to 20 carbon atoms, or $R^7$ and $R^8$ may bond together to form a ring, and in that event, each is an alkylene group of 1 to 20 carbon atoms which may contain a hetero atom such as oxygen, sulfur or nitrogen, "a" is 0 or 1, "b" is an integer of 2 to 4, and X is a valence bond or O.

7. A polymer comprising recurring units of the following general formula (2) and the following general formula (4a) or (4b) and having a weight average molecular weight of 1,000 to 500,000:

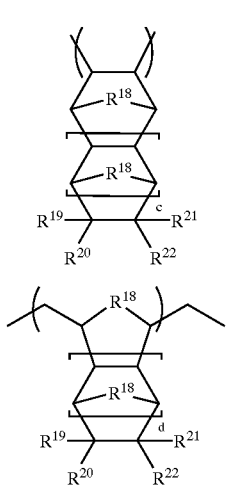

(4a)

(4b)

wherein $R^1$ to $R^3$ each are hydrogen, fluorine or a straight, branched or cyclic alkyl or fluorinated alkyl group of 1 to 20 carbon atoms, $R^4$ is a valence bond or a straight, branched or cyclic alkylene or fluorinated alkylene group of 1 to 20 carbon atoms, $R^5$ is a straight, branched or cyclic fluorinated alkyl group of 4 to 30 carbon atoms, and X is a balence bond or O;

wherein $R^{18}$ is a methylene group, oxygen atom, sulfur atom or $SO_2$, $R^{19}$ to $R^{22}$ each are hydrogen, fluorine, a straight, branched or cyclic alkyl or fluorinated alkyl group of 1 to 20 carbon atoms or $-R^{23}-SO_2R^{24}$, at least one of $R^{19}$ to $R^{22}$ containing $-R^{23}-SO_2R^{24}$, $R^{23}$ is a valence bond or a straight, branched or cyclic alkylene or fluorinated alkylene group of 1 to 20 carbon atoms, $R^{24}$ is a straight, branched or cyclic fluorinated alkyl group of 1 to 20 carbon atoms, c is 0 or 1, and d is an integer of 0 to 2.

8. The polymer of claim 4 having a weight average molecular weight of 2,000 to 100,000.

9. A polymer comprising recurring units of the following general formula (2) and having a weight average molecular weight of 1,000 to 500,000,

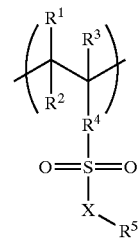

(2)

wherein $R^1$ to $R^3$ each are hydrogen, fluorine or a straight, branched or cyclic alkyl or fluorinated alkyl group of 1 to 20 carbon atoms, $R^4$ is a valence bond or a straight, branched or cyclic alkylene or fluorinated alkylene group of 1 to 20 carbon atoms, $R^5$ is a straight, branched or cyclic fluorinated alkyl group of 4 to 30 carbon atoms, and X is a valence bond or O;

and further comprising recurring units of the following general formula (5):

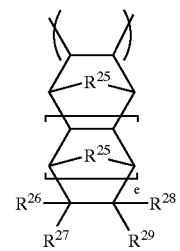

(5)

wherein $R^{25}$ is a methylene group, oxygen atom, sulfur atom or $SO_2$, $R^{26}$ to $R^{29}$ each are hydrogen, fluorine, $-R^{30}-OR^{31}$, $-R^{30}-CO_2R^{31}$ or a straight, branched or cyclic alkyl or fluorinated alkyl group of 1 to 20 carbon atoms, at least one of $R^{26}$ to $R^{29}$ containing $-R^{30}-OR^{31}$ or $-R^{30}-CO_2R^{31}$, $R^{30}$ is a valence bond or a straight, branched or cyclic alkylene or fluorinated alkylene group of 1 to 20 carbon atoms, $R^{31}$ is hydrogen, an acid labile group, adhesive group or a straight, branched or cyclic fluorinated alkyl group of 1 to 20 carbon atoms which may contain a hydrophilic group such as hydroxyl, and e is 0 or 1.

10. The polymer of claim 9 wherein said recurring units of formula (5) have a structure of the following general formula (5a) or (5b):

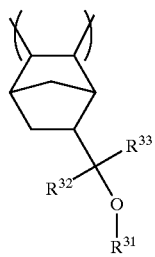

(5a)

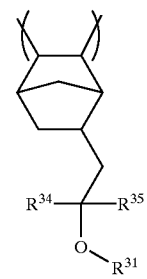

(5b)

wherein $R^{31}$ is as defined above, $R^{32}$ to $R^{35}$ each are hydrogen, fluorine or an alkyl or fluorinated alkyl group of 1 to 4 carbon atoms, at least either one of $R^{32}$ and $R^{33}$ contains at least one fluorine atom, and at least either one of $R^{34}$ and $R^{35}$ contains at least one fluorine atom.

11. A polymer comprising recurring units of the following general formula (2) and having a weight average molecular weight of 1,000 to 500,000,

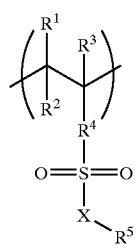

(2)

wherein $R^1$ to $R^3$ each are hydrogen, fluorine or a straight, branched or cyclic alkyl or fluorinated alkyl group of 1 to 20 carbon atoms, $R^4$ is a valence bond or a straight, branched or cyclic alkylene or fluorinated alkylene group of 1 to 20 carbon atoms, $R^5$ is a straight, branched or cyclic fluorinated alkyl group of 4 to 30 carbon atoms, and X is a valence bond or O;

and further comprising recurring units of the following general formula (6):

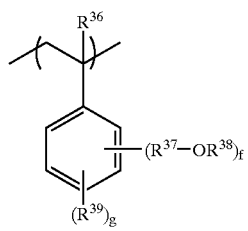

(6)

wherein $R^{36}$ is hydrogen, fluorine or a straight, branched or cyclic alkyl or fluorinated alkyl group of 1 to 20 carbon atoms, $R^{37}$ is a valence bond or a straight, branched or cyclic alkylene or fluorinated alkylene group of 1 to 20 carbon atoms, $R^{38}$ is hydrogen or an acid labile group, $R^{39}$ is fluorine or a straight, branched or cyclic fluorinated alkyl group of 1 to 20 carbon atoms, f is 1 or 2, and g is an integer of 0 to 4, satisfying $1 \leq f+g \leq 5$.

12. The polymer of claim 11 wherein the recurring units of formula (6) have the following formula (6a) or (6b):

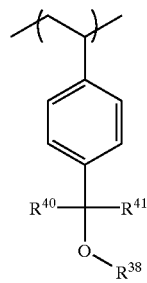

(6a)

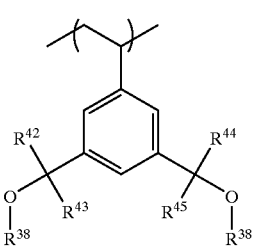

(6b)

wherein $R^{38}$ is as defined above, $R^{40}$ to $R^{45}$ each are hydrogen, fluorine or an alkyl or fluorinated alkyl group of 1 to 4 carbon atoms, at least either one of $R^{40}$ and $R^{41}$ contains at least one fluorine atom, at least either one of $R^{42}$ and $R^{43}$ contains at least one fluorine atom, and at least either one of $R^{44}$ and $R^{45}$ contains at least one fluorine atom.

13. The polymer of claim 4, further comprising recurring units of the following general formula (7):

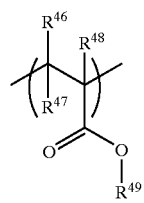

(7)

wherein $R^{46}$ to $R^{48}$ each are hydrogen, fluorine or a straight, branched or cyclic alkyl or fluorinated alkyl group of 1 to 20 carbon atoms, and $R^{49}$ is hydrogen, an acid labile group, an adhesive group or a straight, branched or cyclic fluorinated alkyl group of 1 to 20 carbon atoms which may contain a hydrophilic group such as hydroxyl.

14. The polymer of claim 13 wherein $R^{48}$ in formula (7) is trifluoromethyl.

15. A resist composition comprising the polymer of claim 4.

16. A chemically amplified positive resist composition comprising (A) a the polymer comprising recurring units of the following general formula (2) and having a weight average molecular weight or 1,000 to 500,000,

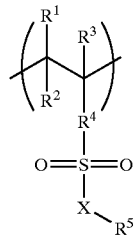

(2)

wherein $R^1$ to $R^3$ each are hydrogen, fluorine or a straight, branched or cyclic alkyl or fluorinated alkyl group of 1 to 20 carbon atoms, $R^4$ is a valence bond or a straight, branched or cyclic alkylene or fluorinated alkylene group of 1 to 20 carbon atoms, $R^5$ is a straight, branched or cyclic fluorinated alkyl group of 4 to 30 carbon atoms, and X is a valence bond or O, and (B) an organic solvent, and (C) a photoacid generator.

17. The resist composition of claim 16, further comprising (D) a basic compound.

18. The resist composition of claim 16, further comprising (E) a dissolution inhibitor.

19. A process for forming a resist pattern comprising the steps of:

applying the resist composition of claim 16 onto a substrate to form a coating, heat treating the coating and then exposing it to high-energy radiation in a wavelength band of 100 to 180 nm or 1 to 30 nm through a photomask, and optionally heat treating the exposed coating and developing it with a developer.

20. The pattern forming process of claim 19 wherein the high-energy radiation is an $F_2$ laser beam, $Ar_2$ laser beam or soft x-ray.

* * * * *